US012735382B2

(12) United States Patent
Omatsu et al.

(10) Patent No.: US 12,735,382 B2
(45) Date of Patent: Sep. 15, 2026

(54) COMPOUND, (CO)POLYMER, COMPOSITION, METHOD FOR FORMING PATTERN, AND METHOD FOR PRODUCING COMPOUND

(71) Applicant: Mitsubishi Gas Chemical Company, Inc., Tokyo (JP)

(72) Inventors: Tadashi Omatsu, Hiratsuka (JP); Masahiro Matsumoto, Niigata (JP); Michihiro Yuri, Niigata (JP); Kentaro Kataoka, Niigata (JP); Takashi Sato, Hiratsuka (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 683 days.

(21) Appl. No.: 17/418,636

(22) PCT Filed: Dec. 23, 2019

(86) PCT No.: PCT/JP2019/050261

§ 371 (c)(1),
(2) Date: Jun. 25, 2021

(87) PCT Pub. No.: WO2020/137935

PCT Pub. Date: Jul. 2, 2020

(65) Prior Publication Data

US 2022/0119336 A1 Apr. 21, 2022

(30) Foreign Application Priority Data

Dec. 27, 2018 (JP) ................................ 2018-244504
Aug. 6, 2019 (JP) ................................ 2019-144313

(51) Int. Cl.

*C07C 69/653* (2006.01)
*G03F 7/004* (2006.01)
*G03F 7/039* (2006.01)
*G03F 7/16* (2006.01)
*G03F 7/20* (2006.01)
*G03F 7/32* (2006.01)
*G03F 7/38* (2006.01)

(52) U.S. Cl.

CPC .......... *C07C 69/653* (2013.01); *G03F 7/0045* (2013.01); *G03F 7/0392* (2013.01); *G03F 7/162* (2013.01); *G03F 7/2004* (2013.01); *G03F 7/322* (2013.01); *G03F 7/38* (2013.01)

(58) Field of Classification Search

None
See application file for complete search history.

(56) References Cited

U.S. PATENT DOCUMENTS 2,100,798 A 11/1937 Dilthey
2,546,872 A 3/1951 Schmid
2,587,437 A 2/1952 Bralley
3,947,468 A 3/1976 Hall
4,017,627 A 4/1977 Sturm
4,252,884 A 2/1981 Bennett
4,289,839 A 9/1981 Dipippo
4,482,489 A 11/1984 Dipippo
4,579,758 A 4/1986 Dorsch
5,332,648 A 7/1994 Kihara
5,986,094 A 11/1999 Ghoshal (Continued)

FOREIGN PATENT DOCUMENTS

CN 1414031 4/2003
CN 1853141 10/2006

(Continued)

OTHER PUBLICATIONS

English language machine generated translation of Masuyama (JP2018095851A, published on Jun. 21, 2018) (Year: 2018).*

CID 86081112, (National Center for Biotechnology Information (2025). PubChem Compound Summary for CID 86081112, (2-Iodophenyl)methyl prop-2-enoate, publicly available on Nov. 3, 2014. Retrieved Jan. 21, 2025 from https://pubchem.ncbi.nlm.nih.gov/compound/2-Iodophenyl_methyl-prop-2-enoate) (Year: 2014).*

(Continued)

*Primary Examiner* — Amy C Bonaparte

(74) *Attorney, Agent, or Firm* — Fitch, Even, Tabin & Flannery LLP

(57) ABSTRACT

The present invention has an object to provide a composition or the like capable of forming a film having high resolution and high sensitivity. The above object can be achieved by the following compound. An iodine-containing (meth)acrylate compound represented by the general formula (1):

(1)

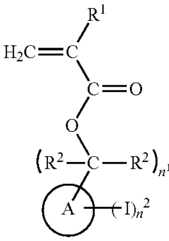

wherein $R^1$ represents a hydrogen atom, a methyl group, or halogen;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A represents an organic group having 1 to 30 carbon atoms;

$n^1$ represents 0 or 1; and $n^2$ represents an integer of 1 to 20.

9 Claims, No Drawings

(56) References Cited

U.S. PATENT DOCUMENTS 6,784,228 B2 8/2004 Ogura
6,794,408 B2 9/2004 Eder
7,871,751 B2 1/2011 Echigo
9,122,153 B2 9/2015 Echigo
9,136,121 B2 9/2015 Hatakeyama
9,274,426 B2 3/2016 Rahman
9,316,913 B2 4/2016 Echigo
9,540,339 B2 1/2017 Echigo
9,904,167 B2 2/2018 Tsuchimura
9,908,831 B2 3/2018 Echigo
9,989,849 B2 6/2018 Nakagawa
10,303,055 B2 5/2019 Sato et al.
10,377,734 B2 8/2019 Echigo
10,495,968 B2 12/2019 Aqad
10,915,021 B2 2/2021 Fukushima
2002/0106909 A1 8/2002 Kato
2003/0092852 A1 5/2003 Ogura
2004/0197709 A1 10/2004 Arase
2004/0229162 A1 11/2004 Ohsawa
2005/0074695 A1 4/2005 Nakamura
2005/0118749 A1 6/2005 Sakamoto et al.
2005/0255712 A1 11/2005 Kato et al.
2006/0094845 A1* 5/2006 Yamamoto ............ G02F 1/3615 526/242
2007/0059632 A1 3/2007 Oguro
2007/0172759 A1 7/2007 Ogihara
2007/0232839 A1 10/2007 Yoshitomo
2008/0113294 A1 5/2008 Echigo
2008/0138744 A1 6/2008 Hatanaka
2008/0153031 A1 6/2008 Echigo et al.
2009/0171061 A1 7/2009 Sue
2009/0246684 A1 10/2009 Kim
2009/0261300 A1 10/2009 Watanabe
2010/0047709 A1 2/2010 Echigo
2010/0081081 A1 4/2010 Enomoto et al.
2010/0099044 A1 4/2010 Hatakeyama
2010/0104977 A1 4/2010 Hatakeyama
2010/0136477 A1 6/2010 Ng
2010/0190107 A1 7/2010 Shibata
2010/0207516 A1 8/2010 Moriwaki
2010/0227859 A1 9/2010 Li
2010/0285407 A1 11/2010 Ogihara
2010/0316950 A1 12/2010 Oguro et al.
2011/0177459 A1 7/2011 Ogihara
2011/0230058 A1 9/2011 Sakamoto
2011/0274713 A1 11/2011 Burn
2011/0311920 A1 12/2011 Kinsho
2012/0064725 A1 3/2012 Kinsho
2012/0171611 A1 7/2012 Ideno et al.
2012/0184103 A1 7/2012 Ogihara
2012/0220112 A1 8/2012 Hatakeyama
2012/0228584 A1 9/2012 Wigglesworth
2013/0004896 A1 1/2013 Echigo
2013/0056653 A1 3/2013 Hatakeyama
2013/0056654 A1 3/2013 Hatakeyama
2013/0084705 A1 4/2013 Nakafuji
2013/0087529 A1 4/2013 Hatakeyama
2013/0150627 A1 6/2013 Okada
2014/0186776 A1 7/2014 Uchiyama
2014/0248556 A1 9/2014 Kato
2014/0248561 A1 9/2014 Echigo
2014/0308615 A1 10/2014 Echigo
2014/0319097 A1 10/2014 Kim
2014/0363768 A1 12/2014 Kinsho
2014/0363955 A1 12/2014 Hatakeyama
2014/0363957 A1 12/2014 Hatakeyama et al.
2014/0363958 A1 12/2014 Hatakeyama
2015/0030980 A1 1/2015 Echigo
2015/0037735 A1 2/2015 Yang
2015/0090691 A1 4/2015 Echigo
2015/0115199 A1 4/2015 Choi et al.
2015/0192851 A1 7/2015 Yamashita et al.
2015/0309403 A1 10/2015 Rahman
2015/0368224 A1 12/2015 Echigo
2015/0376157 A1 12/2015 Echigo
2015/0376158 A1 12/2015 Echigo
2015/0376202 A1 12/2015 Echigo
2016/0130243 A1 5/2016 Satou
2016/0145231 A1 5/2016 Echigo
2017/0183279 A1 6/2017 Echigo
2017/0242338 A1 8/2017 Hirano
2017/0349564 A1 12/2017 Toida
2018/0074402 A1 3/2018 Toida
2018/0074406 A1 3/2018 Toida
2018/0095368 A1 4/2018 Toida et al.
2018/0155472 A1 6/2018 Saha et al.
2018/0208703 A1 7/2018 Okada
2018/0246405 A1 8/2018 Kudo et al.
2018/0246409 A1 8/2018 Toida
2018/0284605 A1* 10/2018 Aqad .................... C07C 69/653
2019/0056657 A1 2/2019 Toida et al.
2019/0094690 A1 3/2019 Hatakeyama et al.
2019/0163065 A1 5/2019 Hatakeyama et al.
2019/0202955 A1 7/2019 Aqad et al.
2020/0026188 A1 1/2020 Maruyama
2020/0209747 A1 7/2020 Hatakeyama et al.
2021/0018841 A1 1/2021 Sato et al.
2021/0116813 A1 4/2021 Sato et al.
2021/0206901 A1 7/2021 Sato et al.
2022/0119336 A1 4/2022 Omatsu et al.

FOREIGN PATENT DOCUMENTS

CN 1942825 A 4/2007
CN 101088046 A 12/2007
CN 101889247 11/2010
CN 102070595 5/2011
CN 103304385 9/2013
CN 103717562 A 4/2014
CN 103733135 A 4/2014
CN 103733136 4/2014
CN 103804196 A 5/2014
CN 104245885 A 12/2014
CN 104557552 A 4/2015
CN 104870438 A 8/2015
CN 105131161 A 12/2015
CN 107428717 A 12/2017
CN 107533291 A 1/2018
CN 108690164 A 10/2018
CN 110325916 A 10/2019
EP 1275673 1/2003
EP 1300403 4/2003
EP 1666970 6/2006
EP 2743249 6/2014
EP 2743769 6/2014
EP 2743770 A1 6/2014
EP 3279190 2/2018
JP S48049508 A 7/1973
JP S61-60630 A 3/1986
JP 62094841 A 5/1987
JP S62191850 A 8/1987
JP H01283280 11/1989
JP H04217675 8/1992
JP H0519463 1/1993
JP H05034913 A 2/1993
JP H05134415 A 5/1993
JP H05163290 A 6/1993
JP 05216235 A 8/1993
JP H06049402 A 2/1994
JP H06242607 A 9/1994
JP H07215833 8/1995
JP H09020721 1/1997
JP H1025220 1/1998
JP H10045764 A 2/1998
JP H11072925 3/1999
JP 2001042525 2/2001
JP 2002214769 7/2002
JP 2002334869 A 11/2002
JP 2002334896 11/2002
JP 2002341542 11/2002
JP 2003201333 7/2003
JP 2004177668 A 6/2004
JP 2004271838 A 9/2004
JP 2005250434 A 9/2005

(56) References Cited

FOREIGN PATENT DOCUMENTS

| | | | | |
|---|---|---|---|---|
| JP | 2005266741 A | | 9/2005 | |
| JP | 2005326838 A | | 11/2005 | |
| JP | 2005326868 A | | 11/2005 | |
| JP | 2005346024 A | | 12/2005 | |
| JP | 2006036648 | | 2/2006 | |
| JP | 2006098869 | | 4/2006 | |
| JP | 2006113136 | | 4/2006 | |
| JP | 2006160663 | | 6/2006 | |
| JP | 2006213634 | | 8/2006 | |
| JP | 2006259482 A | | 9/2006 | |
| JP | 2007019294 | | 1/2007 | |
| JP | 2007199653 | | 8/2007 | |
| JP | 2007226170 A | | 9/2007 | |
| JP | 2007226204 A | | 9/2007 | |
| JP | 2007262398 | | 10/2007 | |
| JP | 2007326847 | | 12/2007 | |
| JP | 2008065081 | | 3/2008 | |
| JP | 2008145539 A | | 6/2008 | |
| JP | 2008201954 A | | 9/2008 | |
| JP | 2008239868 | | 10/2008 | |
| JP | 2009073738 A | | 4/2009 | |
| JP | 2009-098651 A | | 5/2009 | |
| JP | 2009098155 A | | 5/2009 | |
| JP | 2009108313 | | 5/2009 | |
| JP | 2009155256 | | 7/2009 | |
| JP | 2009173623 A | | 8/2009 | |
| JP | 2009-275155 A | | 11/2009 | |
| JP | 2009300978 | | 12/2009 | |
| JP | 2010160189 | | 7/2010 | |
| JP | 2010170013 | | 8/2010 | |
| JP | 2010219295 | | 9/2010 | |
| JP | 2010235643 | | 10/2010 | |
| JP | 2011068624 | | 4/2011 | |
| JP | 2011105887 | | 6/2011 | |
| JP | 2011150023 | | 8/2011 | |
| JP | 20121687 | | 1/2012 | |
| JP | 2012068652 | | 4/2012 | |
| JP | 2012077295 | | 4/2012 | |
| JP | 2012083731 A | | 4/2012 | |
| JP | 2012145897 | | 8/2012 | |
| JP | 2013064978 A | | 4/2013 | |
| JP | 2013068928 | | 4/2013 | |
| JP | 2013083833 A | | 5/2013 | |
| JP | 2013083939 | | 5/2013 | |
| JP | 2013087173 A | | 5/2013 | |
| JP | 2013137524 A | | 7/2013 | |
| JP | 2013253161 A | | 12/2013 | |
| JP | 2014196288 A | | 10/2014 | |
| JP | 2014205746 | | 10/2014 | |
| JP | 2015018220 | | 1/2015 | |
| JP | 2015018221 | | 1/2015 | |
| JP | 2015018223 | | 1/2015 | |
| JP | 2015087115 A | | 5/2015 | |
| JP | 2015514691 A | | 5/2015 | |
| JP | 2015-108781 A | | 6/2015 | |
| JP | 2015-516972 A | | 6/2015 | |
| JP | 2015110532 A | | 6/2015 | |
| JP | 2015127821 | | 7/2015 | |
| JP | 2015161823 A | * | 9/2015 | G03F 7/0045 |
| JP | 2018-013744 A | | 1/2018 | |
| JP | 2018095851 A | * | 6/2018 | |
| JP | 2018-172640 A | | 11/2018 | |
| JP | 2019061217 A | | 4/2019 | |
| JP | 2019101417 A | | 6/2019 | |
| JP | 2020106826 A | | 7/2020 | |
| JP | 2004-029542 A | | 1/2024 | |
| KR | 20060071423 | | 6/2006 | |
| KR | 1020100095563 | | 8/2010 | |
| KR | 1020130025833 A | | 3/2013 | |
| KR | 20130048307 A | | 5/2013 | |
| KR | 1020140066161 | | 5/2014 | |
| KR | 1020140079358 | | 6/2014 | |
| KR | 1020140079359 | | 6/2014 | |
| KR | 10-2017-0133367 A | | 12/2017 | |
| KR | 10-2018-0050665 A | | 5/2018 | |
| KR | 10-2018-0111531 A | | 10/2018 | |
| KR | 10-2019-0035543 A | | 4/2019 | |
| KR | 10-2019-0126090 A | | 11/2019 | |
| TW | 200519538 A | | 6/2005 | |
| TW | 200918502 A | | 5/2009 | |
| TW | 201204450 A | | 2/2012 | |
| TW | 201321362 A | | 6/2013 | |
| TW | 201321891 A | | 6/2013 | |
| TW | 201321895 A | | 6/2013 | |
| TW | 201329031 A | | 7/2013 | |
| TW | 201446711 A | | 12/2014 | |
| TW | 201446825 A | | 12/2014 | |
| TW | 201723663 A | | 7/2017 | |
| TW | 201837048 A | | 10/2018 | |
| TW | 201921109 A | | 6/2019 | |
| TW | 201930283 A | | 8/2019 | |
| WO | 9736960 | | 10/1997 | |
| WO | 0214434 | | 2/2002 | |
| WO | 03017002 | | 2/2003 | |
| WO | 2004066377 A1 | | 8/2004 | |
| WO | 2005029189 A1 | | 3/2005 | |
| WO | 2005111724 | | 11/2005 | |
| WO | 2006068267 A1 | | 6/2006 | |
| WO | 2007097457 | | 8/2007 | |
| WO | 2008053974 A1 | | 5/2008 | |
| WO | 2008/105266 A1 | | 9/2008 | |
| WO | 2008137816 A2 | | 11/2008 | |
| WO | 2009072465 A1 | | 6/2009 | |
| WO | 2009119201 A1 | | 10/2009 | |
| WO | 2009145224 | | 12/2009 | |
| WO | 2011034062 A1 | | 3/2011 | |
| WO | 2012165507 A1 | | 12/2012 | |
| WO | 2013010102 | | 1/2013 | |
| WO | 2013024777 A1 | | 2/2013 | |
| WO | 2013024778 A1 | | 2/2013 | |
| WO | 2013024779 A1 | | 2/2013 | |
| WO | 2013066067 | | 5/2013 | |
| WO | 2013184755 | | 12/2013 | |
| WO | 2014050690 | | 4/2014 | |
| WO | 2014123032 A1 | | 8/2014 | |
| WO | 2014199660 | | 12/2014 | |
| WO | 2017/043561 A1 | | 3/2017 | |
| WO | 2018/180049 A1 | | 10/2018 | |
| WO | 2019151403 | | 8/2019 | |
| WO | 2019/208762 A1 | | 10/2019 | |
| WO | 2019208761 A1 | | 10/2019 | |
| WO | 2020040161 A1 | | 2/2020 | |
| WO | 2020137935 A1 | | 7/2020 | |
| WO | 2021029396 A1 | | 2/2021 | |

OTHER PUBLICATIONS

Machine generated English language translation of JP2015161823A, obtained Jan. 2025 (Year: 2025).*

Saha, et al., Radiopaque Resists for Two-Photon Lithography to Enable Submicron 3D Imaging of Polymer Parts via X-ray Computed Tomography, ACS Appl. Mater. Interfaces, 2018, vol. 10 (No. 1), pp. 1164-1172.

International Search Report for PCT/JP2019/050261, mailed Mar. 24, 2020, and English Translation submitted herewith (9 pages).

Green, O. et al., "Near-Infrared Dioxetane Luminophores with Direct Chemiluminescence Emission Mode," Journal of the American Chemical Society, 2017, vol. 139 (16 pages).

Okazaki, S. et al., "Development of Lithography Technology in These 40 Years," S&T Publishing Inc., Dec. 2016, pp. 1-21. (Cited in Specification).

Saha, S.K. et al., "Radiopaque Resists for Two-Photon Lithography to Enable Submicron 3D Imaging of Polymer Parts via X-ray Computed Tomography," Applied Materials Interfaces, 2018, vol. 10, pp. 1164-1172.

Shinji Okazaki et al., Development Lithography Technology in These 40 Years, S&T Publishing Inc., Dec. 9, 2016.

H. Yamamoto et al., Jpn.J.Appl.Phys.46,L142 (2007).

H. Yamamoto et al., J.Vac.Sci.Technol.b; 23,2728 (2005).

International Search Report for PCT/JP2021/003658, mailed Apr. 27, 2021, and English Translation submitted herewith (7 pages).

(56) References Cited

OTHER PUBLICATIONS

International Search Report for PCT/JP2021/018110, mailed Jul. 3, 2021, and English Translation submitted herewith (7 pages).
Shinji Okazaki et al., "New Trends of Photoresists", CMC Publishing Co., Ltd., Sep. 2009, p. 211-259.
Ahmed Munir et al., The Direct Bradsher Reaction. Part I. Synthesis of Thiophen Analogues of Linear Polycyclic Hydrocarbons, Journal of the Chemical Society, Perkin Transactions 1,1973, pp. 1099-1103.
Areephong, Jetsuda, et al., "A concise synthesis of functionalized 7-oxa-[5]-helicenes," Tetrahedron Letters, 2004, vol. 45, pp. 3067-3070.
Bentley, K. W., and Robinson, R., "A Synthesis of alpha-Anhydrotrimethylbrazilone," Tetrahedron Letters, 1959, vol. 1, Issue 2, pp. 11-14.
Brecher, Jonathan, Graphical Representation Standards for Chemical Structure Diagrams, Pure Appl. Chem., 2008, pp. 277-410, vol. 80, No. 2, Cambridge, Massachusetts.
Burnett, James C., et al. "Novel small molecule inhibitors of botulinum neurotoxin A metalloprotease activity," Biochemical and Biophysical Research Communications, vol. 310, No. 1, Oct. 2003, pp. 84-93.
Cameron, Donald W., et al., "Synthesis of a natural polychloro dinaphthofuran quinone," Tetrahedron Letters, 1980, vol. 21(14), pp. 1385-1386.
Chatterjea, J.N., "Experiments on the Syntheses of Furano Compounds. Part XII. Further Transformations of isoCoumaranone," Journal of the Indian Chemical Society, 1957, vol. 34, Issue 4, pp. 299-305,.
Clowes, G. A., et al., "Studies of the Scholl reaction: Oxidative Dehydrogenation involving 1- Ethoxynaphthylenen and Related Compounds," J Chem. Soc (C) 2519-2526 (1968).
Dann, von Otto, and HOFMANN, Hans, Synthese von ()-Brasilin, Justus Liebigs Annalen der Chemie, 1963, vol. 667, Issue 1, pp. 116-125.
English Translation of JP H01-283280 A, Nov. 14, 1989.
European Journal of Medicinal Chemistry, published bi-monthly, Ejmcs, 13(4): 381-385 (1978).
Ghodratbeigi Mohsen et al., "Design, modeling and synthesis of molecular tweezers with self-assembly Properties," Journal of Molecular Structure, 2011, vol. 990, No. 1, pp. 140-151.
Hagihara K. et al., "The effect of Ti-addition on plastic deformation and fracture behavior of directionally solidified NliAl/Cr(Mo) eutetic alloys," Intermetallics, 2006, vol. 14, No. 10, pp. 1326-1331.
Hannuksela, Miska M et al., "Hook for scalable extensions: video parameter set," Joint Collaborative Team on Video Coding (JCT-VC) of ITU-T SG 16 WP 3 and ISO/IEC JTC 1/SC 29/WG 11, May 2012, pp. 1-6.
International Preliminary Report on Patentability issued in International Application No. PCT/JP2012/070304. 2012.
International Search Report date of mailing Feb. 25, 2014 for PCT/JP2014/051775 and English translation of the same (4 pages).
International Search Report date of mailing Feb. 9, 2016, for PCT/JP2015/084907 and English translation of the same (7 pages).
International Search Report dated Mar. 25, 2014 for International Application No. PCT/JP2014/052524 with English Translation (8 pages).
International Search Report dated May 13, 2014 for International Application No. PCT/JP2014/052530 with English Translation (8 pages).
International Search Report dated Oct. 23, 2012 issued in International Application No. PCT/JP2012/070304.
International Search Report dated Sep. 11, 2012 for International Application No. PCT/JP2012/070305 with English Translation (5 pages).
International Search Report on Patentability for PCT/JP2016/056333 mailed May 24, 2016; English translation submitted herewith (7 pages).
JHA Amitabh and BEAL Jennifer, "Convenient synthesis of 12H-benzo[a]xanthenes from 2-tetralone," Tetrahedron Letters, 2004, vol. 45, No. 49, pp. 8999-9001.
Journal of the Chemical Society, p. 5336-5341 (Nov. 1963).
Luo, Junfei et al., "Salicylic acids as readily available starting materials for the synthesis of meta-substituted biaryls," ChemComm, 2015, vol. 51, pp. 3127-3130.
Machine English Translation of JP 2008-239868 A, Oct. 9, 2008.
Massif, Cedrik, et al. "New insights into the water-solubilisation of fluorophores by post-synthetic 'click' and Sonogashira reactions," Organic & Biomolecular Chemistry, vol. 10, No. 22, Apr. 2012, pp. 4430-4336.
Nakayama, Tomonari, Nomura, Masayoshi, Haga, Kohji, and Ueda, Mitsuru, A New Three-Component Photoresist Based on Calix[4]resorcinarene Derivative, a Cross-Linker, and a Photo-acid Generator, The Chemical Society of Japan, Bulletin of the Chemical Society of Japan, 1998, vol. 71, No. 12, pp. 2979-2984.
Nature, 161:930-931 (1948).
Nishiyama Tomihiro et al., Antioxidant activities of fused heterocyclic compounds, xanthene-2,7- diols with BHT or Catechol skeleton, Polymer Degradation and Stability, 1998, vol. 62, No. 3, pp. 529-534.
Ohishi Takeshi. Tetrahedron Letters 42 (2001) 2493-2496.
Osman A-M, Reactions Between Chloro-p-benzoquinones and Beta-Naphtol, Journal of Organic Chemistry, 1957, vol. 22, pp. 342-344.
Percec, Virgil, et al., Synthesis of Aromatic Polyethers by Scholl Reaction. I. Poly(1,1'-Dinaphthyl Ether Phenyl Sulfone)s and Poly(1,1'-Dinaphthyl Ether Phenyl Ketone)s, Journal of Polymer Science: Part A: Polymer Chemistry, 1988, vol. 26, pp. 783-805.
Percec, Virgil, et al., "Synthesis of Aromatic Polyethers by Scholl Reaction. VI. Aromatic Polyethers by Cation-Radical Polymerization of 4,4'-, 3,3'-, and 2-2'-Bis(1-naphthoxy)biphenyls and of 1,3-Bis(1-naphthoxy)benzene," Macromolecules, 1992, vol. 25(1), pp. 64-74.
Protiva, Miroslav et al., Potential metabolites of tricyclic neuroleptics: 2,8-dihydroxy and 3,8-dihydroxy derivatives of 10-(4-methylpiperazino)-10,11-dihydrodibenzo[b, fJthiepin, Part CXXXIII in the series Neurotropic and Psychotropic Agents, Collection of Czechoslovak Chemical Communications, 1979, vol. 44, No. 10, pp. 2987-2996.
Protiva, Miroslav, et al., "Potential metabolites or tricyclic neuroleptics" 3,7-dimethoxy and 7,8-dimethoxy derivatives of 10-{4-methylpiperazino )-10,11-dihydrodibenzo[b,f]thiepin, Collection of Czechoslovak Chemical Communications, 1981, vol. 46, pp. 1808-1817.
Singh Ritesh and Panda Gautam, "Scandium triflate-catalyzed one-pot domino approach towards general and efficient syntheses of unsymmetrical 9-substituted xanthene derivatives," Organic & Biomolecular Chemistry, 2010, vol. 8, No. 5, pp. 1097-1105.
Sirkecioglu Okan et al., A Novel Synthesis of 14-(Hydroxymethylalkyl) Derivatives of Dibenzoxanthenes and 3,3-Dimethyl-4-(2-hydroxy-1-naphthyl)benzo[fJchroman, Journal of Heterocyclic Chemistry, Mar. 1, 1998, vol. 35, No. 2, pp. 457-460.
Sirringhaus Henning et al., Dibenzothienobisbenzothiophene—a novel fused-ring oligomer with high field-effect mobility, Journal of Materials Chemistry, 1999, vol. 9, pp. 2095-2101.
Skandinavisches Archiv fuer Physiologie, 43: 215-243 (1923).
Tian- jun Liu, Ke-shen Zhang, Yong-jun Chen, Dong Wang and Chao-jun Li, "Chiral Conjugated Oligomer Based On 1, 1'-BINOL With 3, 3 ' -Acetylene -Phenylene- Acetylene Spacer", Chinese Journal of Polymer Science, Mar. 8, 2001, vol. 19, No. 5, p. 521-526.
Written Opinion of the International Searching Authority issued in International Application No. PCT/JP2012/070304 (including translation), dated Oct. 23, 2012.
International Search Report on Patentability for PCT/JP2016/056332 mailed May 31, 2016; English translation submitted herewith (11 pages).
Jayakrishnan et al., "Synthesis and Polymerization of Some lodine-Containing Monomers for Biomedical Applications", Journal of Applied Polymer cience, vol. 44, pp. 743-748 (1992).

(56) References Cited

OTHER PUBLICATIONS

Moszner et al., "Synthesis and polymerization of hydrophobic iodine-containing methacrylaes", Die Angewandte Makromolekulare Chemie 224(1995) 115-123 (nr. 3917).
Wang et al., "Radio-opaque Micelles for X-ray Imaging", Aust. J. Chem., 2014, 67, pp. 78-84.
Okamura et al., "Synthesis and properties of radiopaque polymer hydrogels II: copolymers of 2,4,6-triiodophenyl-or-N-(3-carboxy-2,4,6,-triiodophenyl)-acrylamide and p-styrene sufonate", Journal of Molecular Structure , vol. 602-603, 2002, 17-28.
Zaharia et al., "Triiodophenyl acrylate-based microbeads find important use in the medical field", Int. J. Nano and Biomaterials, vol. 3, No. 4, 2011.
Artola et al., "Elimination of barium sulphate from acrylic bone cements. Use of two-iodone-containing monomers", Biomaterials vol. 24 (2003) 4071-4080.
Schmidt et al., "Synthesis of 8-Aryl-Substituted Coumarins Based on Ring-Closing Metathesis and Suzuki-Miyaura Coupling: SYnthesis of a Furyl Coumarin Natural Product from Galipea panamensis", The Journal of Organic Chemistry 2012, vol. 77, 2360-2367.
Kruft et al., "Studies on two new radiopaque polymeric biomaterials", Journal of Biomedical Materials Research, vol. 28, 1259-1266 (1994).

* cited by examiner

COMPOUND, (CO)POLYMER, COMPOSITION, METHOD FOR FORMING PATTERN, AND METHOD FOR PRODUCING COMPOUND

CROSS-REFERENCE TO RELATED APPLICATIONS

This application is a U.S. national phase application filed under 35 U.S.C. § 371 of International Application Number PCT/JP2019/050261, filed Dec. 23, 2019, designating the United States, which claims priority from Japanese Application Number 2019-144313, filed Aug. 6, 2019, and claims priority from Japanese Application Number 2018-244504, filed Dec. 27, 2018.

FIELD OF THE INVENTION

The present invention relates to a compound, a (co) polymer, a composition, a method for forming a pattern, and a method for producing a compound.

BACKGROUND OF THE INVENTION

In recent years, in the production of semiconductor elements and liquid crystal display elements, semiconductors (patterns) and pixels have been rapidly miniaturized due to the advance in lithography technology. As an approach for pixel miniaturization, the exposure light source has been shifted to have a shorter wavelength, in general. Specifically, ultraviolet rays typified by g-ray and i-ray have been used conventionally, but nowadays, far ultraviolet exposure such as KrF excimer laser (248 nm) and ArF excimer laser (193 nm) is being the center of mass production. Furthermore, the introduction of extreme ultraviolet (EUV) lithography (13.5 nm) is progressing. In addition, electron beam (EB) is also used for forming a fine pattern.

Up to now, typical resist materials are polymer based resist materials capable of forming an amorphous film. Examples include polymer based resist materials such as polymethyl methacrylate, polyhydroxy styrene with an acid dissociation group, and polyalkyl methacrylate (see, for example, Non Patent Literature 1).

Conventionally, a line pattern of about 10 to 100 nm is formed by irradiating a resist thin film made by coating a substrate with a solution of these resist materials with ultraviolet, far ultraviolet, electron beam, extreme ultraviolet or the like.

In addition, lithography using electron beam or extreme ultraviolet has a reaction mechanism different from that of normal photolithography. Furthermore, lithography with electron beam or extreme ultraviolet aims at forming fine patterns of several nm to ten-odd nm. Accordingly, there is a demand for a resist material having higher sensitivity for an exposing source when the resist pattern dimension is reduced. In particular, lithography with extreme ultraviolet is required to further increase sensitivity in terms of throughput.

As a resist material that solves the problems as mentioned above, an inorganic resist material having a metallic element such as titanium, tin, hafnium and zirconium has been proposed (see, for example, Patent Literature 1).

CITATION LIST

Patent Literature

Patent Literature 1: Japanese Patent Laid-Open No. 2015-107781

Non Patent Literature

Non Patent Literature 1: Shinji Okazaki et al., "Development of Lithography Technology in These 40 Years", S&T Publishing Inc., Dec. 9, 2016

SUMMARY OF INVENTION

However, conventionally developed resist compositions have problems such as many film defects, insufficient sensitivity, insufficient etching resistance, or poor resist pattern. In particular, it is required to achieve both high resolution and high sensitivity.

In view of the above circumstances, the present invention has an object to provide a composition capable of forming a film having high resolution and high sensitivity, as well as a method for forming a resist pattern and a method for forming an insulating film, using the composition.

The inventors have, as a result of devoted examinations to solve the problems mentioned above, found out that a compound and (co)polymer having a specific structure have high solubility in a safe solvent, and are capable of forming a film having high resolution and high sensitivity when the compound and the like are used in a composition for film formation purposes for photography or film formation purposes for resist, leading to completion of the present invention.

More specifically, the present invention is as follows.

[1]

An iodine-containing (meth)acrylate compound represented by the general formula (1):

(1)

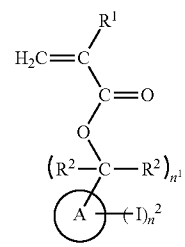

wherein $R^1$ represents a hydrogen atom or a methyl group or a halogen group;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A represents an organic group having 1 to 30 carbon atoms;

$n^1$ represents 0 or 1; and $n^2$ represents an integer of 1 to 20.

[1-1]

The iodine-containing (meth)acrylate compound according to [1], wherein $n^1$ is 0, and A is an alicyclic ring having 5 to 30 carbon atoms and optionally having a substituent.

[1-2]

The iodine-containing (meth)acrylate compound according to [1-1], wherein the alicyclic ring having 5 to 30 carbon atoms and optionally having a substituent is an adamantane ring optionally having a substituent.

[2]

The iodine-containing (meth)acrylate compound according to [1], wherein the general formula (1) is the general formula (2):

(2)

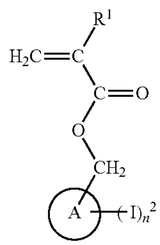

wherein $R^1$, A, and $n^2$ are as defined in [1].

[3]

The iodine-containing (meth)acrylate compound according to [2], wherein the general formula (2) is the general formula (3):

(3)

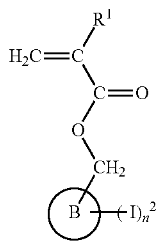

wherein

B represents an organic group containing an aromatic ring and having 5 to 30 carbon atoms; and $R^1$ and $n^2$ are as defined in [1].

[3-1]

The iodine-containing (meth)acrylate compound according to [3], wherein B is an aromatic ring having 5 to 30 carbon atoms and optionally having a substituent.

[3-2]

The iodine-containing (meth)acrylate compound according to [3-1], wherein the aromatic ring having 5 to 30 carbon atoms and optionally having a substituent is a benzene ring optionally having a substituent.

[4]

The iodine-containing (meth)acrylate compound according to [2], wherein the general formula (2) is the general formula (3'):

(3)

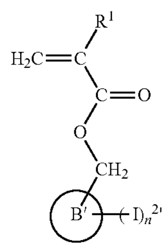

wherein

B' represents an organic group containing an alicyclic ring and having 5 to 30 carbon atoms; and $R^1$ and $n^2$ are as defined in [1].

[4-1]

The iodine-containing (meth)acrylate compound according to [4], wherein B' is an alicyclic ring having 5 to 30 carbon atoms and optionally having a substituent.

[4-2]

The iodine-containing (meth)acrylate compound according to [4-1], wherein the alicyclic ring having 5 to 30 carbon atoms and optionally having a substituent is an adamantane ring optionally having a substituent.

[5]

The iodine-containing (meth)acrylate compound according to any one of [1] to [4], wherein $n^2$ represents an integer of 2 to 20.

[6]

An iodine-containing (meth)acrylate (co)polymer comprising a repeating unit represented by the general formula (4).

(4)

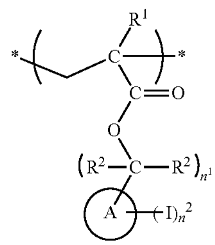

wherein $R^1$ represents a hydrogen atom, a methyl group, or halogen;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A represents an organic group having 1 to 30 carbon atoms;

$n^1$ represents 0 or 1;

$n^2$ represents an integer of 1 to 20; and symbol * represents a bonding site to an adjacent repeating unit.

[6-1]

The iodine-containing (meth)acrylate (co)polymer according to [6], wherein $n^1$ is 0, and A is an alicyclic ring having 5 to 30 carbon atoms and optionally having a substituent.

[6-2]

The iodine-containing (meth)acrylate (co)polymer according to [6-1], wherein the alicyclic ring having 5 to 30 carbon atoms and optionally having a substituent is an adamantane ring optionally having a substituent.

[7]

The iodine-containing (meth)acrylate (co)polymer according to [6], wherein the general formula (4) is the general formula (5):

(5)

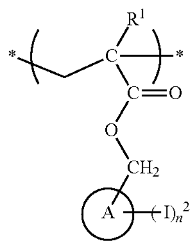

wherein $R^1$, $n^2$, A, and symbol * are as defined in [6].

[8]

The iodine-containing (meth)acrylate (co)polymer according to [7], wherein the general formula (5) is the general formula (6):

(6)

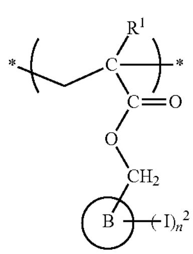

wherein

B represents an organic group containing an aromatic ring and having 5 to 30 carbon atoms; and $R^1$, $n^2$, and symbol * are as defined in [6].

[8-1]

The iodine-containing (meth)acrylate (co)polymer according to [8], wherein B is an aromatic ring having 5 to 30 carbon atoms and optionally having a substituent.

[8-2]

The iodine-containing (meth)acrylate (co)polymer according to [8-1], wherein the aromatic ring having 5 to 30 carbon atoms and optionally having a substituent is a benzene ring optionally having a substituent.

[9]

The iodine-containing (meth)acrylate (co)polymer according to [7], wherein the general formula (5) is the general formula (6'):

(6)

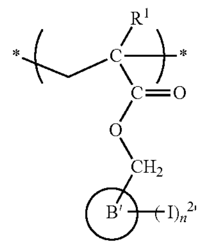

wherein

B' represents an organic group containing an alicyclic ring and having 5 to 30 carbon atoms; and $R^1$, $n^2$, and symbol * are as defined in [6].

[9-1]

The iodine-containing (meth)acrylate (co)polymer according to [9], wherein B' is an alicyclic ring having 5 to 30 carbon atoms and optionally having a substituent.

[9-2]

The iodine-containing (meth)acrylate (co)polymer according to [9-1], wherein the alicyclic ring having 5 to 30 carbon atoms and optionally having a substituent is an adamantane ring optionally having a substituent.

[10]

The iodine-containing (meth)acrylate (co)polymer according to any one of [6] to [9-2], wherein $n^2$ represents an integer of 2 to 20.

[11]

A composition comprising the iodine-containing (meth) acrylate (co)polymer according to any one of [6] to [10].

[12]

The composition according to [11], further comprising a solvent.

[13]

The composition according to [11] or [12], further comprising an acid generating agent.

[14]

The composition according to any one of [11] to [13], further comprising an acid diffusion controlling agent.

[15]

A method for forming a pattern, comprising the steps of:

forming a film using the composition according to any one of [11] to [14];

exposing the film; and forming a pattern by removing an exposed portion of the exposed film by using a developer.

[16]

A method for producing the iodine-containing (meth) acrylate compound according to [1], comprising the step of reacting an iodine-containing hydroxy compound represented by the general formula (a) with a (meth)acrylic acid compound represented by the general formula (b):

(a)

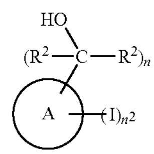

wherein $R^2$, A, $n^1$, and $n^2$ are as defined in [1].

(b)

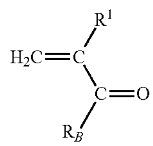

wherein $R^1$ is as defined in [1]; and $R_B$ is selected from the group consisting of a hydroxyl group, a halogen atom, and an (meth)acryloyloxy group.

[16-1]

The method for producing the iodine-containing (meth) acrylate compound according to [16], wherein $n^1$ is 0, and A is an alicyclic ring having 5 to 30 carbon atoms and optionally having a substituent.

[16-2]

The method for producing the iodine-containing (meth) acrylate compound according to [16-1], wherein the alicyclic ring having 5 to 30 carbon atoms and optionally having a substituent is an adamantane ring optionally having a substituent.

[17]

The method for producing the iodine-containing (meth) acrylate compound according to [16], wherein the general formula (a) is the general formula (a1):

(a1)

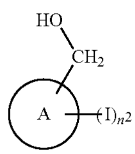

wherein A and $n^2$ are as defined in [1].

[18]

The method for producing the iodine-containing (meth) acrylate compound according to [16], wherein the general formula (a) is the general formula (a2):

(a2)

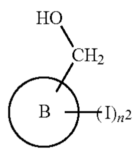

wherein

B represents an organic group containing an aromatic ring and having 5 to 30 carbon atoms; and $R^2$ is as defined in [1].

[18-1]

The method for producing the iodine-containing (meth) acrylate compound according to [18], wherein B is an aromatic ring having 5 to 30 carbon atoms and optionally having a substituent.

[18-2]

The method for producing the iodine-containing (meth) acrylate compound according to [18-1], wherein the aromatic ring having 5 to 30 carbon atoms and optionally having a substituent is a benzene ring optionally having a substituent.

[19]

The method for producing the iodine-containing (meth) acrylate compound according to [16], wherein the general formula (a) is the general formula (a3):

(a3)

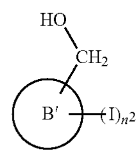

wherein

B' represents an organic group containing an alicyclic ring and having 5 to 30 carbon atoms; and $R^2$ is as defined in [1].

[19-1]

The method for producing the iodine-containing (meth) acrylate compound according to [19], wherein B' is an alicyclic ring having 5 to 30 carbon atoms and optionally having a substituent.

[19-2]

The method for producing the iodine-containing (meth) acrylate compound according to [19-1], wherein the alicyclic ring having 5 to 30 carbon atoms and optionally having a substituent is an adamantane ring optionally having a substituent.

[20]

The method for producing the iodine-containing (meth) acrylate compound according to any one of [16] to [19-2], wherein $n^2$ represents an integer of 2 to 20.

[21]

An iodine-containing hydroxy compound represented by the general formula (a):

(a)

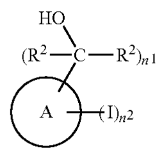

wherein each $R^2$ independently represents a hydrogen atom, a linear organic group having 1 to 20 carbon atoms, a branched organic group having 3 to 20 carbon atoms, or a cyclic organic group having 3 to 20 carbon atoms;

A represents an organic group having 1 to 30 carbon atoms;

$n^1$ represents 0 or 1; and $n^2$ represents an integer of 1 to 20.

[21-1]

The iodine-containing hydroxy compound according to [21], wherein $n^1$ is 0, and A is an alicyclic ring having 5 to 30 carbon atoms and optionally having a substituent.

[21-2]

The iodine-containing hydroxy compound according to [21-2], wherein the alicyclic ring having 5 to 30 carbon atoms and optionally having a substituent is an adamantane ring optionally having a substituent.

[22]

The iodine-containing hydroxy compound according to [21], wherein the general formula (a) is the general formula (a1):

(a1)

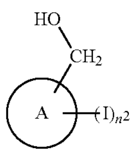

wherein

A and $n^2$ are as defined in [21].

[23]

The iodine-containing hydroxy compound according to [22], wherein the general formula (a1) is the general formula (a2):

(a2)

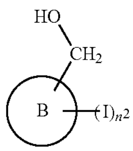

wherein

B represents an organic group containing an aromatic ring and having 5 to 30 carbon atoms; and $R^2$ is as defined in [21].

[23-1]

The iodine-containing hydroxy compound according to [23], wherein B is an aromatic ring having 5 to 30 carbon atoms and optionally having a substituent optionally having a substituent.

[23-2]

The iodine-containing hydroxy compound according to [23-1], wherein the aromatic ring having 5 to 30 carbon atoms and optionally having a substituent is a benzene ring optionally having a substituent.

[24]

The iodine-containing hydroxy compound according to [22], wherein the general formula (a1) is the general formula (a3):

(a3)

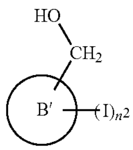

wherein

B' represents an organic group containing an alicyclic ring and having 5 to 30 carbon atoms; and $n^2$ is as defined in [21].

[24-1]

The iodine-containing hydroxy compound according to [24], wherein B is an alicyclic ring having 5 to 30 carbon atoms and optionally having a substituent.

[24-2]

The iodine-containing hydroxy compound according to [24], wherein the alicyclic ring having 5 to 30 carbon atoms and optionally having a substituent is an adamantane ring optionally having a substituent.

[25]

The iodine-containing hydroxy compound according to any one of [21] to [24-2], wherein $n^2$ represents an integer of 2 to 20.

[26]

The method for producing the iodine-containing (meth) acrylate compound according to [16], further comprising the step of performing an iodine introduction reaction to a compound represented by the following general formula (Sa1) or general formula (Sa2):

(Sa1)

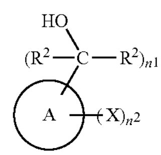

wherein $R^2$, A, $n^1$, and $n^2$ are as defined in [1]; and

X is selected from the group consisting of a hydroxy group; an aliphatic group having 1 to 30 carbon atoms or an aromatic group, the aliphatic group or the aromatic group having at least one selected from the group consisting of a hydroxy group, an aldehyde group and a carboxyl group; or a halogen group.

(Sa2)

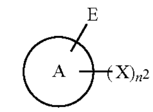

wherein A and $n^2$ are as defined in [1];

X is as defined in the formula (Sa1); and

E is a hydrocarbon group having 1 to 30 carbon atoms and having at least one selected from the group consisting of a hydroxy group, an aldehyde group, a carboxyl group, an ether group, a thiol group, and an amino group.

According to the present invention, it is possible to provide a compound and a composition capable of forming a film having high resolution and sensitivity, as well as a method for forming a resist pattern and a method for forming an insulating film, using these.

DESCRIPTION OF EMBODIMENTS

Hereinafter, an embodiment of the present invention will be described (hereinafter, may be referred to as the "present embodiment"). The present embodiment is given in order to illustrate the present invention. The present invention is not limited to only the present embodiment.

In the present specification, the (meth)acrylate means acrylate and methacrylate. Other terms having the expression (meth) shall be construed in the same manner as (meth)acrylate.

In the present specification, the (co)polymer means a homopolymer and a copolymer.

[Iodine-Containing (Meth)Acrylate Compound]

An iodine-containing (meth)acrylate compound of the present invention is a compound represented by the following formula (1):

(1)

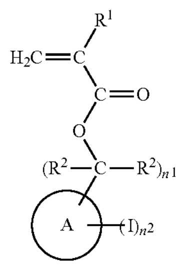

In the formula (1), $R^1$ represents a hydrogen atom or a methyl group or a halogen group;

each $R^2$ independently represents a hydrogen atom, a linear organic group having 1 to 20 carbon atoms, a branched organic group having 3 to 20 carbon atoms, or a cyclic organic group having 3 to 20 carbon atoms;

A represents an organic group having 1 to 30 carbon atoms;

$n^1$ represents 0 or 1; and $n^2$ represents an integer of 1 to 20.

As $R^1$, a hydrogen atom or a methyl group or a halogen group can be used. As the halogen group, publicly known atoms can be used, and F, Cl, Br, I or the like can be appropriately used. $R^1$ is preferably a methyl group or a halogen group from the viewpoint of exposure sensitivity and material stability when the compound of the present invention is used as a constituent unit of resin for resists, more preferably a halogen group and still more preferably I, from the viewpoint of exposure sensitivity.

$R^2$ may be a combination of two or more selected from the group consisting of a linear organic group having 1 to 20 carbon atoms, a branched organic group having 3 to 20 carbon atoms, and a cyclic organic group having 3 to 20 carbon atoms.

$R^2$ is preferably a hydrogen atom for the purpose of suppressing an increase in Tg of the resin and improving the effect of introducing the iodine element. Further, for the purpose of controlling solubility in the developer, it is preferable to use an organic group having 1 or more carbon atoms in order to improve the acid decomposability. It is also preferable to use a hydrogen atom for the purpose of suppressing acid decomposability, especially ensuring solubility in an alkali developer and suppressing residue.

$R^2$ may have a substituent. Examples of $R^2$ include, for example, an alkyl group having 1 to 20, 1 to 10, or 1 to 6 carbon atoms, which may have a substituent; an alkenyl group having 2 to 20, 2 to 10, or 2 to 6 carbon atoms, which may have a substituent; an alkynyl group having 2 to 20, 2 to 10, or 2 to 6 carbon atoms, which may have a substituent; a cycloalkyl group having 3 to 20, 3 to 10, or 3 to 6 carbon atoms, which may have a substituent; a cycloalkenyl group having 3 to 20, 3 to 10, or 3 to 6 carbon atoms, which may have a substituent; a cycloalkynyl group having 3 to 20, 3 to 10, or 3 to 6 carbon atoms, which may have a substituent; an aryl group having 5 to 20, 5 to 10, or 5 to 6 carbon atoms, which may have a substituent; and combinations thereof.

Specific examples of $R^2$ include, for example, a methyl group, an ethyl group, a propyl group, a butyl group, a pentyl group, a hexyl group, a heptyl group, an octyl group, a nonyl group, a decyl group, an icosyl group, a cyclopropyl group, a cyclobutyl group, a cyclopentyl group, a cyclohexyl group, a cycloheptyl group, a cyclooctyl group, a cyclononyl group, a cyclodecyl group, a cycloicosyl group, an adamantyl group, an ethylene group, a propylene group, a butylene group, a phenyl group, a naphthyl group, an anthracene group, a phenanthrene group, a tetracene group, a chrysene group, a triphenylene group, a pyrene group, a benzopyrene group, an azulene group, and a fluorene group, which may have a substituent. These may each contain an ether bond, a ketone bond or an ester bond.

Here, the groups listed above include isomers. For example, the propyl group includes a n-propyl group and an isopropyl group, and the butyl group includes a n-butyl group, a sec-butyl group, an isobutyl group, and a tert-butyl group.

Examples of the substituent for $R^2$ include, but are not particularly limited to, a halogen atom, a hydroxy group, a cyano group, a nitro group, an amino group, a thiol group, a heterocyclic group, a linear aliphatic hydrocarbon group, a branched aliphatic hydrocarbon group, a cyclic aliphatic hydrocarbon group, an aryl group, an aralkyl group, an alkoxy group, an alkenyl group, an acyl group, an alkoxycarbonyl group, an alkyloyloxy group, an aryloyloxy group, an alkylsilyl group, and various crosslinkable groups and acid dissociation groups.

The "crosslinkable group" refers to a group capable of crosslinking by acid, alkali, light or heat in the presence of a catalyst or without a catalyst. Examples of the crosslinkable group include, but not particularly limited to, a group having an allyl group, a group having a (meth)acryloyl group, a group having an epoxy (meth)acryloyl group, a group having a urethane (meth)acryloyl group, a group having a hydroxy group, a group having a glycidyl group, a group having a vinyl containing phenylmethyl group, a group having a styrene group, a group having an alkynyl group, a group having a carbon-carbon double bond, a group having a carbon-carbon triple bond, and a group containing these groups.

The "acid dissociation group" is a group that is cleaved in the presence of an acid to generate an alkali soluble group (for example, a phenolic hydroxy group, a carboxyl group, a sulfonic acid group, or a hexafluoroisopropanol group) or the like. The acid dissociation group is not particularly limited, but can be arbitrarily selected for use from among, for example, those proposed in hydroxystyrene resins, (meth)acrylic acid resins, and the like for use in chemically amplified resist compositions for KrF or ArF. Specific examples of the acid dissociation group include, for example, those described in International Publication No. WO 2016/158168.

A may have a substituent. Examples of the compound serving as the skeleton of A include, for example, an alkane group having 1 to 30, 1 to 20, 1 to 10, or 1 to 6 carbon atoms, which may have a substituent; an alkene group having 2 to 30, 2 to 20, 2 to 10, or 2 to 6 carbon atoms, which may have a substituent; an alkyne group having 2 to 30, 2 to 20, 2 to 10, or 2 to 6 carbon atoms, which may have a substituent; a cycloalkane group having 3 to 30, 3 to 20, 3 to 10, or 3 to 6 carbon atoms, which may have a substituent; a cycloalkene group having 3 to 30, 3 to 20, 3 to 10, or 3 to 6 carbon atoms, which may have a substituent; a cycloalkyne group having 3 to 30, 3 to 20, 3 to 10, or 3 to 6 carbon atoms, which may have a substituent; an arene group having 5 to 30, 5 to 20, 5 to 10, or 5 to 6 carbon atoms, which may have a substituent; and combinations thereof.

Specific examples of the compound serving as the skeleton of A include, for example, methane, ethane, propane, butane, pentane, hexane, heptane, octane, nonane, decane, icosane, triacontane, cyclopropane, cyclobutane, cyclopentane, cyclohexane, cycloheptane, cyclooctane, cyclononane, cyclodecane, cycloicosane, cyclotriacontane, adamantane, ethylene, propylene, butene, pentene, hexene, heptene, octene, nonene, decene, icosene, triacontene, benzene, phenol, naphthalene, anthracene, phenanthrene, tetracene, chrysene, triphenylene, pyrene, pentacene, benzopyrene, coronene, azulene, and fluorene, which may have a substituent, and combinations thereof. These may each contain an ether bond, a ketone bond or an ester bond.

Examples of the substituent for the compound serving as the skeleton of A include, but are not particularly limited to, a halogen atom (fluorine, chlorine, bromine), a hydroxy group, a cyano group, a nitro group, an amino group, a thiol group, a heterocyclic group, a linear aliphatic hydrocarbon group, a branched aliphatic hydrocarbon group, a cyclic aliphatic hydrocarbon group, an aryl group, an aralkyl group, an alkoxy group, an alkenyl group, an acyl group, an alkoxycarbonyl group, an alkyloyloxy group, an aryloyloxy group, an alkylsilyl group, and various crosslinkable groups and acid dissociation groups.

The "crosslinkable group" and the "acid dissociation group" are not particularly limited, and for example, those described for $R^2$ can be used.

$n^1$ represents 0 or 1, and is preferably 1.

$n^2$ is an integer of 1 to 20, preferably an integer of 2 to 20, more preferably an integer of 2 to 10, and still more preferably an integer of 2 to 5.

The compound represented by the formula (1) is preferably a compound represented by the formula (2) from the viewpoint of reactivity.

(2)

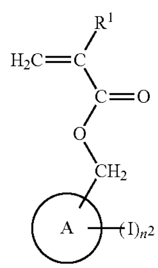

In the formula (2), $R^1$, A, and $n^2$ are as defined in the formula (1).

The compound represented by the formula (1) is more preferably a compound represented by the formula (3) from the viewpoint of etching resistance.

(3)

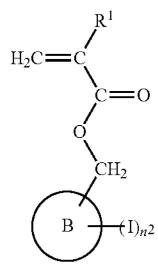

In the formula (3), B represents an organic group containing an aromatic ring and having 5 to 30 carbon atoms, and $R^1$ and $n^2$ are as defined in the formula (1).

B may have a substituent. Examples of the compound serving as the skeleton of B include, for example, an arene having 5 to 30 carbon atoms, 5 to 20 carbon atoms, 5 to 10 carbon atoms, or 5 to 6 carbon atoms, which may have a substituent.

Specific examples of the compound serving as the skeleton of B include, for example, benzene, phenol, naphthalene, anthracene, phenanthrene, tetracene, chrysene, triphenylene, pyrene, pentacene, benzopyrene, coronene, azulene, fluorene, and combinations thereof, which may have a substituent. These may each contain an ether bond, a ketone bond or an ester bond.

Examples of the substituent for the compound serving as the skeleton of B include, but are not particularly limited to, a halogen atom (fluorine, chlorine, bromine), a hydroxy group, a cyano group, a nitro group, an amino group, a thiol group, a heterocyclic group, a linear aliphatic hydrocarbon group, a branched aliphatic hydrocarbon group, a cyclic aliphatic hydrocarbon group, an aryl group, an aralkyl group, an alkoxy group, an alkenyl group, an acyl group, an alkoxycarbonyl group, an alkyloyloxy group, an aryloyloxy group, an alkylsilyl group, and various crosslinkable groups and acid dissociation groups, and a hydroxy group or an acid dissociation group is preferable.

The "crosslinkable group" and the "acid dissociation group" are not particularly limited, and for example, those described for $R^2$ can be used. Although not particularly limited, the acid dissociation group bonded to the aromatic ring of B is preferably a group that is cleaved in the presence of an acid to generate a hydroxy group.

The compound represented by the formula (1) is more preferably a compound represented by the formula (3') from the viewpoint of etching resistance.

(3')

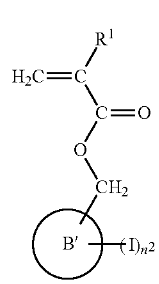

In the formula (3), B' represents an organic group containing an alicyclic ring and having 5 to 30 carbon atoms, and $R^1$ and $n^2$ are as defined in the formula (1).

B' may have a substituent. Examples of the compound serving as the skeleton of B' include, for example, a cycloalkane having 5 to 30, 5 to 20, 5 to 10 or 5 to 6 carbon atoms, which may have a substituent; a cycloalkene having 5 to 30, 5 to 20, 5 to 10 or 5 to 6 carbon atoms, which may have a substituent; and a cycloalkyne having 5 to 30, 5 to 20, 5 to 10 or 5 to 6 carbon atoms, which may have a substituent; and combinations thereof.

Specific examples of the compound serving as the skeleton of B' include, for example, cyclopentane, cyclohexane, cycloheptane, cyclooctane, cyclononane, cyclodecane, cycloicosane, cyclotriacontane, and adamantane, which may have a substituent, and combinations thereof. These may each contain an ether bond, a ketone bond or an ester bond.

Examples of the substituent for the compound serving as the skeleton of B' include, but are not particularly limited to, a halogen atom (fluorine, chlorine, bromine), a hydroxy group, a cyano group, a nitro group, an amino group, a thiol group, a heterocyclic group, a linear aliphatic hydrocarbon group, a branched aliphatic hydrocarbon group, a cyclic aliphatic hydrocarbon group, an aryl group, an aralkyl group, an alkoxy group, an alkenyl group, an acyl group, an alkoxycarbonyl group, an alkyloyloxy group, an aryloyloxy group, an alkylsilyl group, and various crosslinkable groups and acid dissociation groups.

The "crosslinkable group" and the "acid dissociation group" are not particularly limited, and for example, those described for $R^2$ can be used.

Specific examples of the iodine-containing (meth)acrylate compound of the present invention are shown below, but the present invention is not limited thereto. In the following examples, $R^1$ represents a hydrogen atom or a methyl group.

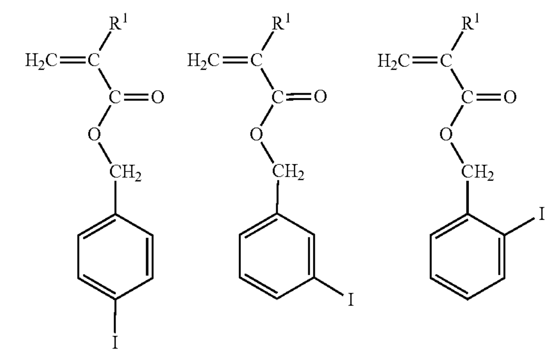

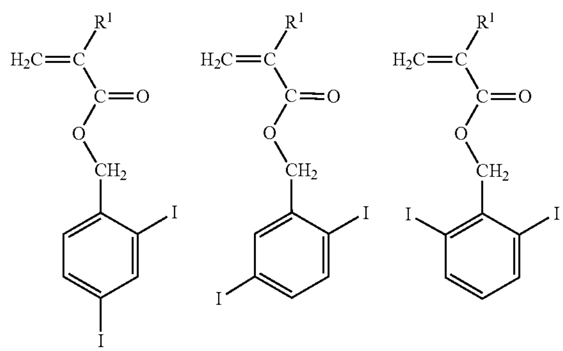

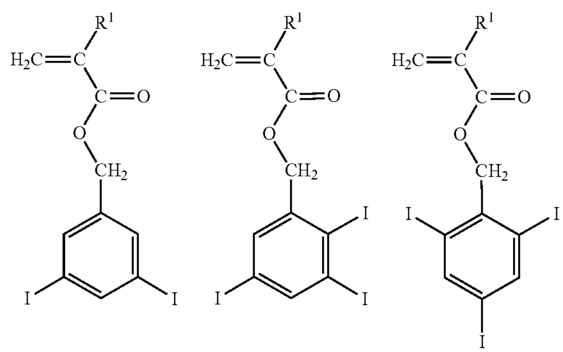

-continued

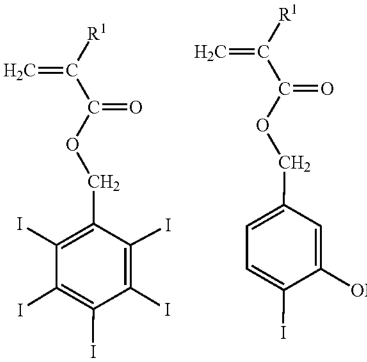

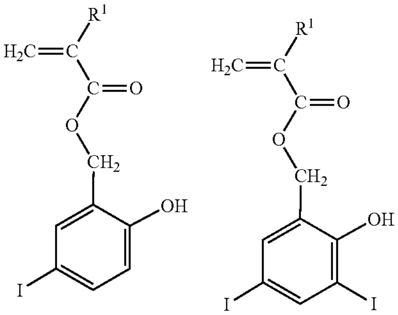

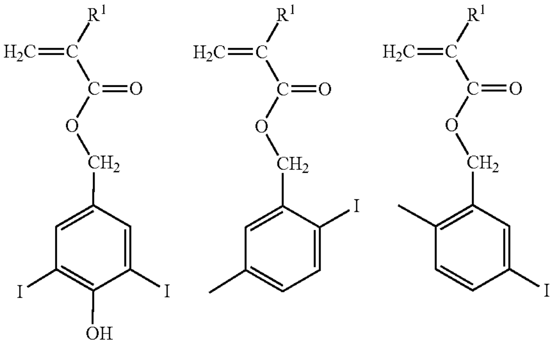

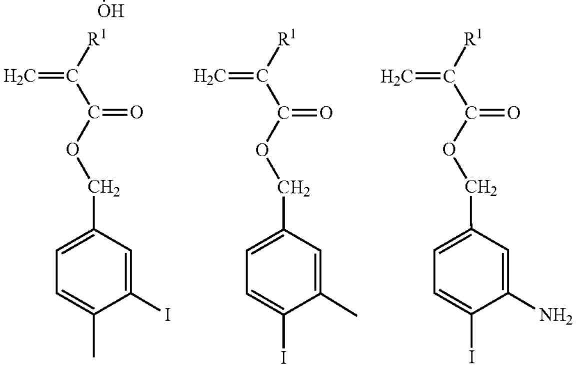

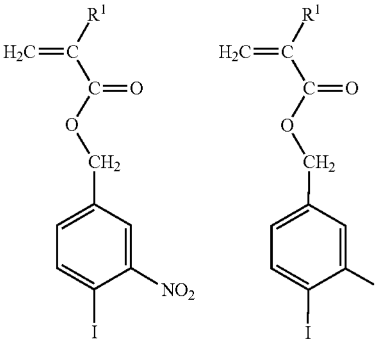

-continued
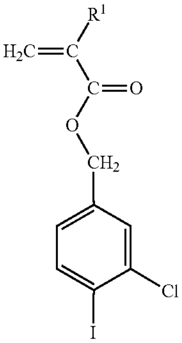
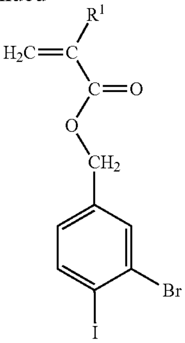
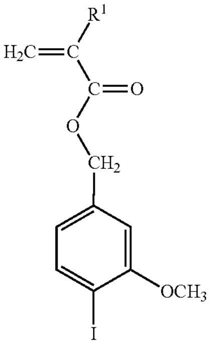
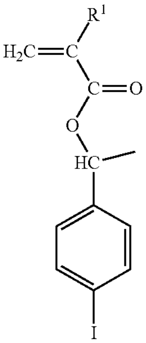
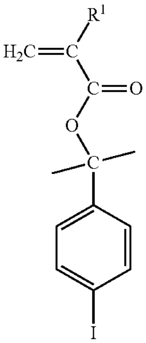
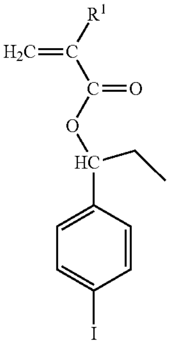
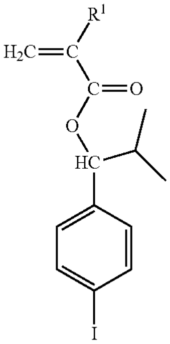
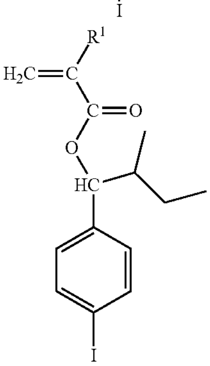
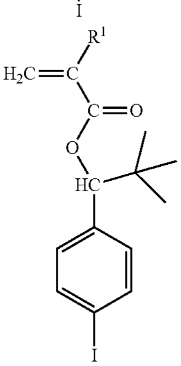
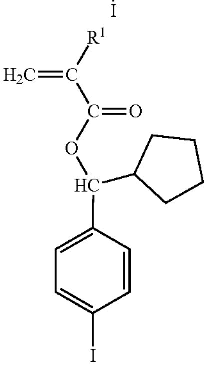
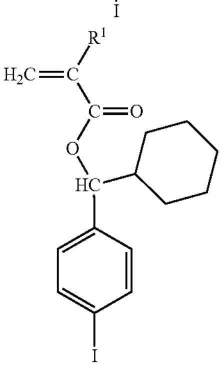
-continued
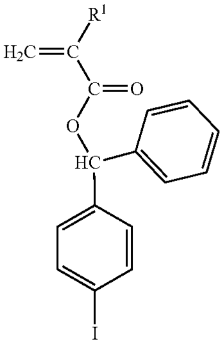
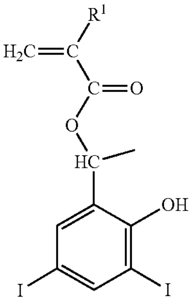
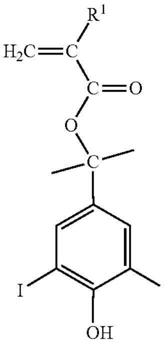
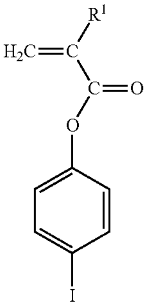
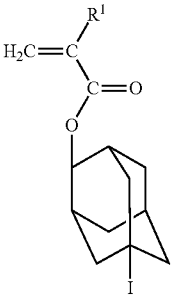
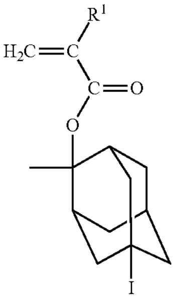
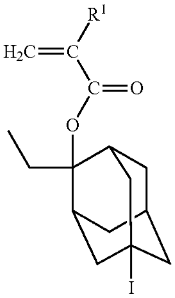
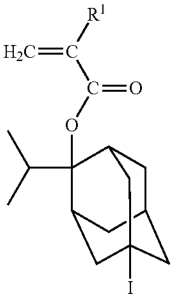
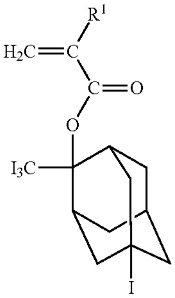
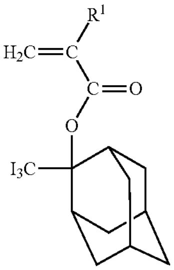

-continued
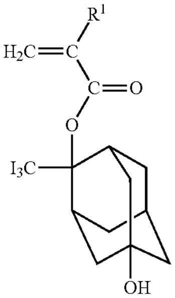
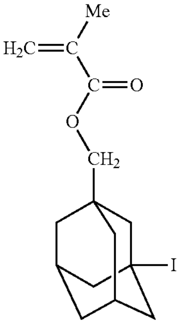
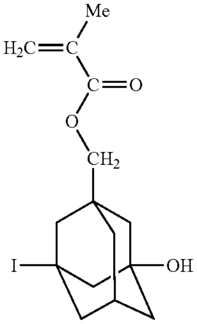
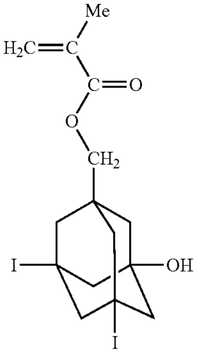
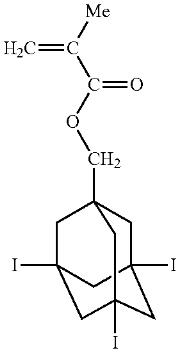
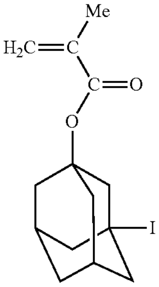
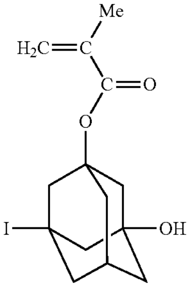
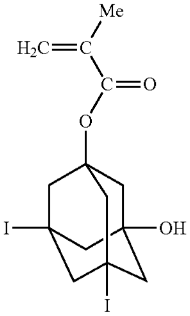
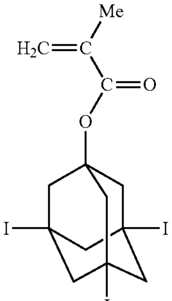
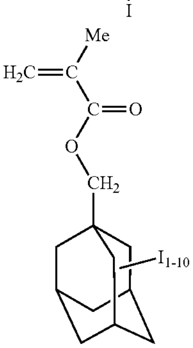
-continued
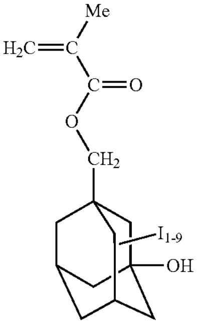
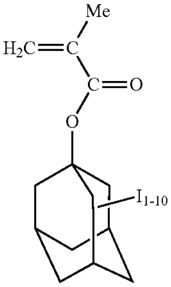
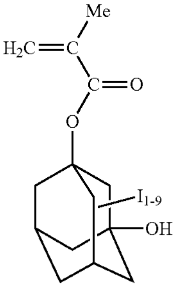
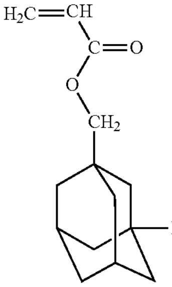
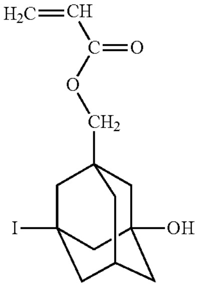
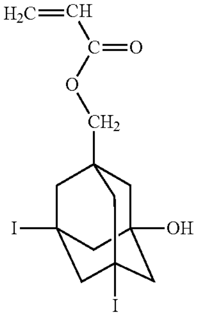
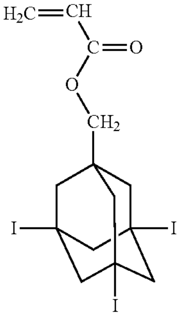
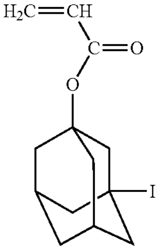
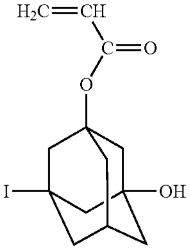
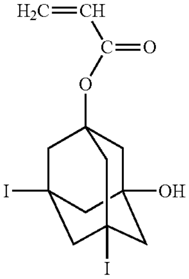
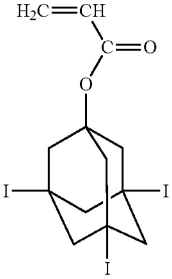

-continued
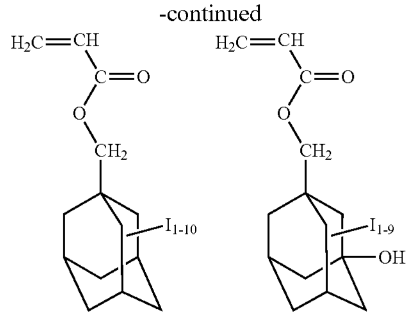
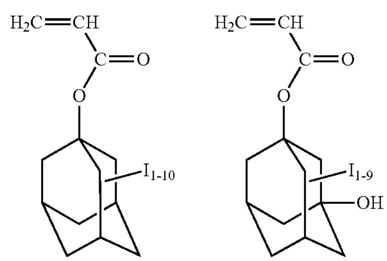
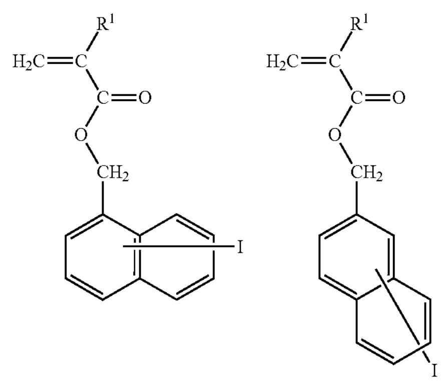
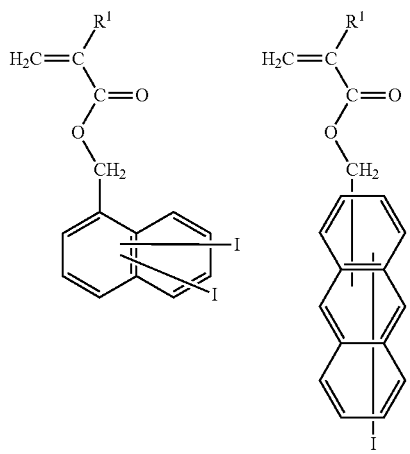
-continued
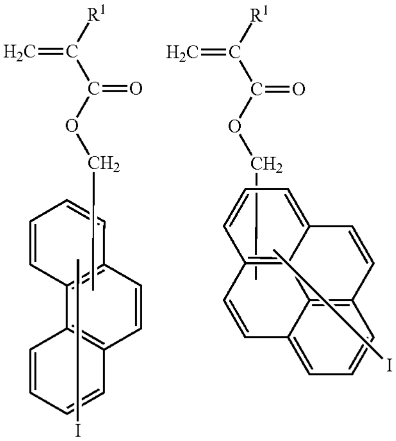
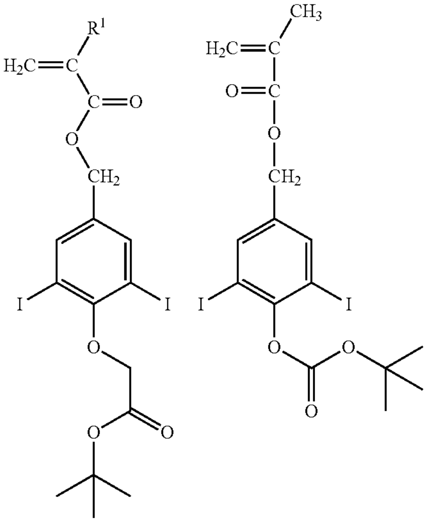
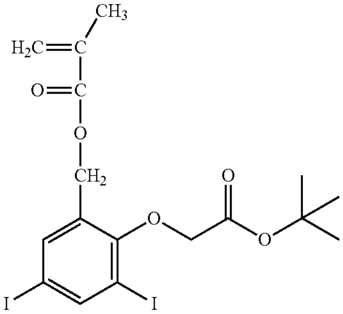
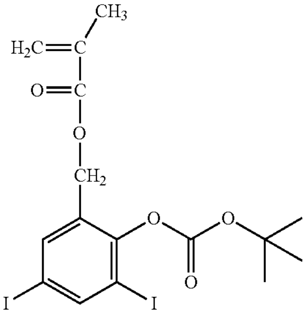

-continued

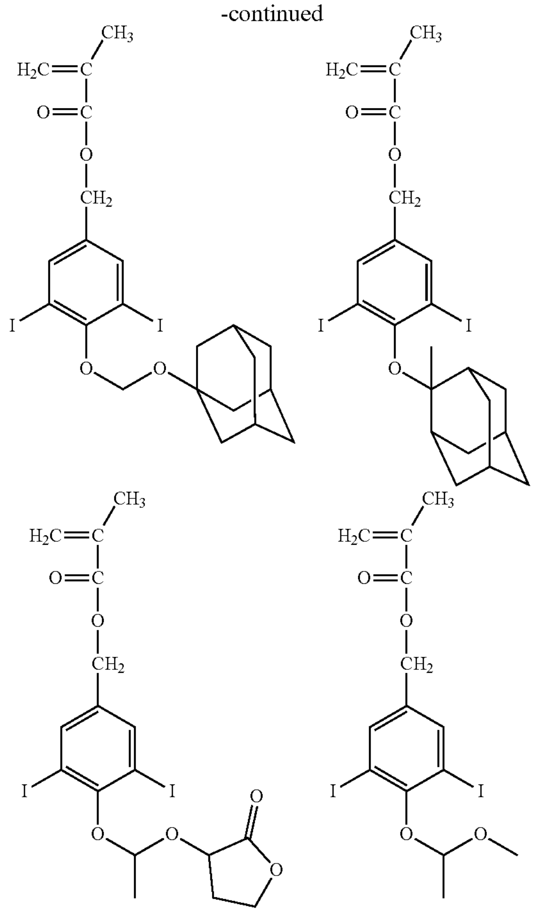

As for structural formulas described in the present specification, for example, when a line indicating a bond to C is in contact with a ring A and a ring B as described below, C is meant to be bonded to either the ring A or the ring B.

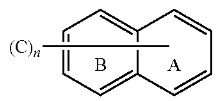

The iodine-containing (meth)acrylate compound represented by the formula (1) of the present invention can be synthesized by a publicly known method. Examples thereof include, but not limited to, a method of reacting an iodine-containing hydroxy compound represented by the general formula (a) with a (meth)acrylic acid compound represented by the general formula (b):

(a)

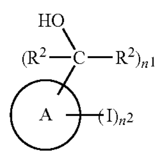

(In the formula (a), $R^2$, A, $n^1$, and $n^2$ are as defined in the formula (1).)

(b)

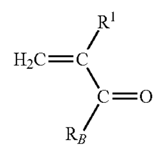

(In the formula (b), $R^1$ is as defined in the formula (1); $R_B$ is selected from the group consisting of a hydroxyl group, a halogen atom, and an (meth)acryloyloxy group; and $R_B$ is preferably a halogen atom such as chlorine atom.)

The compound represented by the general formula (a) is preferably a compound represented by the general formula (a1).

(a1)

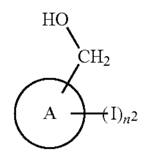

(In the formula (a1), A and $n^2$ are as defined in the formula (1).)

The compound represented by the general formula (a) is preferably a compound represented by the general formula (a2).

(a2)

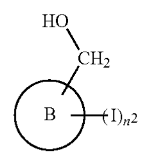

(In the formula (a2),

B represents an organic group containing an aromatic ring and having 5 to 30 carbon atoms; and $n^2$ is as defined in the formula (1).)

The compound represented by the general formula (a) is preferably a compound represented by the general formula (a3).

(a3)

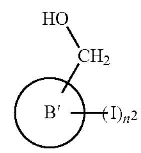

(In the formula (a3),

B' represents an organic group containing an alicyclic ring and having 5 to 30 carbon atoms; and $n^2$ is as defined in the formula (1).)

Examples of the (meth)acrylic acid compound represented by the general formula (b) of the present invention are listed below.

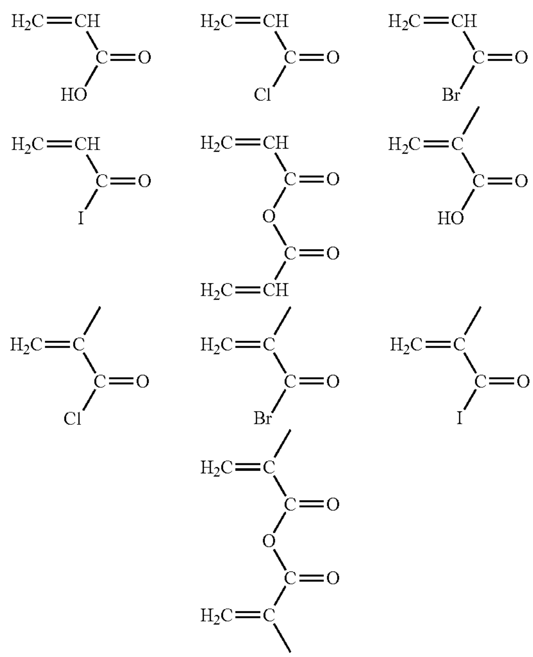

Among these (meth)acrylic acid compounds, (meth) acrylic acid chloride is preferable from the viewpoint of reactivity.

Next, a method for synthesizing an iodine-containing hydroxy compound represented by the general formula (a) will be described. An example of the synthesis of the iodine-containing hydroxy compound represented by the general formula (a) includes performing an iodine introduction reaction to a compound represented by the general formula (Sa1) or (Sa2). When an iodine introduction reaction is performed to the compound of the general formula (Sa2), the method further comprises a step of converting the iodine-introduced product into the compound of the general formula (a):

(Sa1)

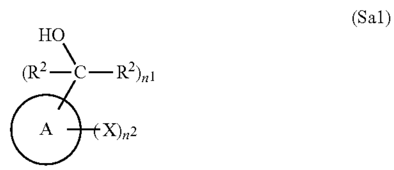

(In the formula (Sa1), $R^2$, A, $n^1$, and $n^2$ are as defined in the formula (1); and X may be selected from the group consisting of a hydroxy group; an aliphatic group having 1 to 30 carbon atoms or an aromatic group, the aliphatic group or the aromatic group having at least one selected from the group consisting of a hydroxy group, an aldehyde group and a carboxyl group; or a halogen group (F, Cl, Br, or the like).)

(Sa2)

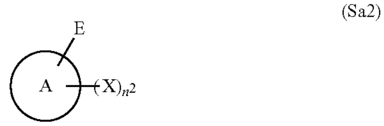

(In the formula (Sa2), A and $n^2$ are as defined in the formula 1;

X is as defined in the formula (Sa1); and

E is a hydrocarbon group having 1 to 30 carbon atoms and having at least one selected from the group consisting of a hydroxy group, an aldehyde group, a carboxyl group, an ether group, a thiol group, and an amino group.)

As the iodine introduction reaction, Sandmeyer method, Halex method, iodine introduction method using an iodinating agent or a compound serving as an iodine source, iodine introduction method using an iodinating agent or a compound serving as an iodine source and an oxidizing agent, iodine introduction method using an iodinating agent or a compound serving as an iodine source and a radical generating agent, iodine introduction method using a system in which catalytic activity is improved by an iodinating agent or a compound serving as an iodine source and zeolite or the like, a method in which iodination is carried out by substitution reaction with a functional group such as a hydroxy group or a halogen group, and the like can be arbitrarily used.

As the iodinating agent, a publicly known compound serving as an iodine supply source such as iodine, potassium iodide, HI, iodine chloride, or N-iodosuccinimide can be arbitrarily used. As the oxidizing agent, a publicly known oxidizing agent such as hydrogen peroxide, iodic acid, periodic acid and sulfuric acid can be used.

Next, a method for producing the iodine-containing (meth)acrylate compound represented by the general formula (1) will be described. The iodine-containing hydroxy compound represented by the general formula (a) is used in an amount of, for example, 0.5 to 100 molar equivalents, preferably 1 to 20 molar equivalents, and still more preferably 1.2 to 5 molar equivalents, based on the (meth)acrylic acid compound represented by the general formula (b). Within this range, the reaction proceeds sufficiently, and the yield of the iodine-containing (meth)acrylate compound represented by the general formula (1), which is the objective product, is high and thus preferable.

As the solvent used in this reaction, solvents that are generally available can be used. For example, an alcohol, an ether, a hydrocarbon, an aromatic solvent, a halogen-based solvent, or the like can be appropriately used as long as the reaction is not inhibited. A mixture of a plurality of solvents may be used as long as the reaction is not inhibited. Since water inhibits the reaction, it is preferable to use a dehydrated solvent.

In addition, as the solvent used in the production of the (meth)acrylate compound containing iodine of the present invention, a solvent having good solubility is preferably used for the purpose of improving the stability of the material and the efficiency in the process from the reaction to the acquisition of the final compound. As a preferable solvent, γP and γH in Hansen Solubility Parameters (A User's Handbook, CRC Press, Boca Raton FL, 2007) can be used as indices, and γP and γH can be determined from the compound structure. γP and γH are preferably lower, and the γP value is preferably 6 or less, more preferably 4 or less, and still more preferably 2 or less. Further, the γH value is preferably 6 or less, more preferably 4 or less, and still more preferably 2 or less. As a particularly preferable solvent, an aromatic solvent such as benzene, toluene or xylene, an aliphatic hydrocarbon-based solvent such as hexane, heptane or octane, or a halogen-based solvent such as dichloromethane or dichloroethane is preferably used as a main solvent.

The reaction temperature and the reaction time depend on the substrate concentration and the catalyst used, but in general, the reaction can be carried out at a reaction temperature of −20° C. to 100° C. for a reaction time of 1 hour to 10 hours under normal pressure, reduced pressure or increased pressure. The reaction can be carried out by arbitrarily selecting a publicly known method such as a batch system, a semi-batch system, or a continuous system.

In addition, a polymerization inhibitor may be added to the series of reactions, and commercially available products that are generally available can be used. Examples thereof include nitroso compounds such as 2,2,6,6-tetramethyl-4-hydroxypiperidine-1-oxyl, N-nitrosophenylhydroxylamine ammonium salt, N-nitrosophenylhydroxylamine aluminum salt, N-nitroso-N-(1-naphthyl)hydroxylamine ammonium salt, N-nitrosodiphenylamine, N-nitroso-N-methylaniline, nitrosonaphthol, p-nitrosophenol, and N,N'-dimethyl-p-nitrosoaniline, sulfur-containing compounds such as phenothiazine, methylene blue and 2-mercaptobenzimidazole, amines such as N,N'-diphenyl-p-phenylenediamine, N-phenyl-N'-isopropyl-p-phenylenediamine, 4-hydroxydiphenylamine and aminophenol, quinones such as hydroxyquinoline, hydroquinone, methylhydroquinone, p-benzoquinone and hydroquinone monomethyl ether, phenols such as p-methoxyphenol, 2,4-dimethyl-6-t-butylphenol, catechol, 3-s-butylcatechol, and 2,2-methylenebis-(6-t-butyl-4-methylphenol), imides such as N-hydroxyphthalimide, oximes such as cyclohexane oxime and p-quinonedioxime, and dialkylthiodipropionate. The amount added is, for example, 0.001 to 10 parts by mass, or preferably 0.01 to 1 part by mass based on 100 parts by mass of the (meth)acrylic acid compound represented by the general formula (b).

The iodine-containing (meth)acrylate compound represented by the general formula (1) obtained by the reaction can be isolated and purified as a desired high-purity monomer by a publicly known purification method such as a separation and purification method using filtration, concentration, distillation, extraction, crystallization, recrystallization, column chromatography, activated carbon, or the like, or a method using a combination thereof.

[Iodine-Containing (Meth)Acrylate (Co)Polymer]

By forming a polymer containing the compound of the present invention as a polymerization unit, a polymer containing one or more halogen elements, one or more hydrophilic groups or one or more decomposable groups can be formed. As a result, a resist composition comprising a polymer containing the compound of the present invention as a constituent unit as a resin component can achieve high sensitivity in a lithography process and high resolution by increasing the solubility contrast of the resin in development.

The iodine-containing (meth)acrylate (co)polymer of the present invention has a repeating unit represented by the following formula (4).

(4)

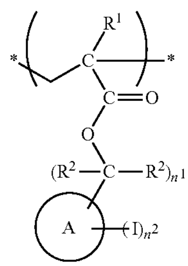

In the formula (4), $R^1$, $R^2$, A, $n^1$, and $n^2$ are as defined in the formula (1), and symbol * represents a bonding site to an adjacent repeating unit.

The iodine-containing (meth)acrylate (co)polymer represented by formula (4) can be obtained by polymerizing one or more iodine-containing (meth)acrylate compounds represented by the general formula (1) of the present invention, or by polymerizing one or more iodine-containing (meth) acrylate compounds represented by the general formula (1) of the present invention with other monomers. The iodine-containing (meth)acrylate (co)polymer can be used as a material for film formation for lithography.

Repeating units other than the repeating unit represented by the formula (4) in the iodine-containing (meth)acrylate copolymer represented by the formula (4) are not particularly limited, but for example, those described in International Publication No. WO 2016/125782, International Publication No. WO 2015/115613, Japanese Patent Laid-Open No. 2015/117305, International Publication No. WO 2014/175275, and Japanese Patent Laid-Open No. 2012/162498, or compounds represented by the formulae (C1) and (C2) below can be used.

(C1)

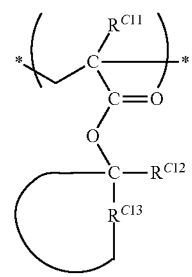

(In the formula (C1), $R^{c11}$ represents hydrogen or a methyl group;

$R^{c12}$ represents hydrogen or an alkyl group having 1 to 4 carbon atoms;

$R^{c13}$ together with the carbon atom to which $R^{c13}$ is bonded represents a cycloalkyl group or a heterocycloalkyl group having 4 to 20 carbon atoms; and a point * represents a bonding site with an adjacent repeating unit.)

Preferably, $R^{c12}$ represents hydrogen or an alkyl group having 1 to 3 carbon atoms, and $R^{c13}$ together with the carbon atom to which $R^{c13}$ is bonded is a cycloalkyl group or a heterocycloalkyl group having 4 to 10 carbon atoms. $R^{13}$ may have a substituent (for example, an oxo group).

(C2)

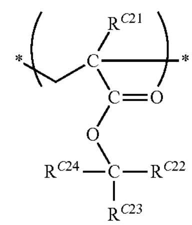

(In the formula (C2), $R^{c21}$ represents hydrogen or a methyl group;

$R^{c22}$ and $R^{c23}$ each independently represent an alkyl group having 1 to 4 carbon atoms;

$R^{c24}$ represents an alkyl group having 1 to 4 carbon atoms or a cycloalkyl group having 5 to 20 carbon atoms;

two or three of $R^{c22}$ to $R^{c24}$ may form an alicyclic structure having 3 to 20 carbon atoms together with the carbon atom to which they are bonded; and a point * represents a bonding site with an adjacent repeating unit.)

Preferably, $R^{c22}$ represents an alkyl group having 1 to 3 carbon atoms, and $R^{c24}$ represents a cycloalkyl group having 5 to 10 carbon atoms. The alicyclic structure formed by $R^{c22}$ to $R^{c24}$ may include a plurality of rings such as an adamantyl group. The alicyclic structure may have a substituent (for example, a hydroxy group or an alkyl group).

Examples of the monomer raw material of the repeating unit represented by the general formula (C2) include, but are not limited to, 2-methyl-2-(meth)acryloyloxyadamantane, 2-ethyl-2-(meth)acryloyloxyadamantane, 2-isopropyl-2-(meth)acryloyloxyadamantane, 2-n-propyl-2-(meth)acryloyloxyadamantane, 2-n-butyl-2-(meth)acryloyloxyadamantane, 1-methyl-1-(meth)acryloyloxycyclopentane, 1-ethyl-1-(meth)acryloyloxycyclopentane, 1-methyl-1-(meth)acryloyloxycyclohexane, 1-ethyl-1-(meth)acryloyloxycyclohexane, 1-methyl-1-(meth)acryloyloxycycloheptane, 1-ethyl-1-(meth)acryloyloxycycloheptane, 1-methyl-1-(meth)acryloyloxycyclooctane, 1-ethyl-1-(meth)acryloyloxycyclooctane, 2-ethyl-2-(meth)acryloyloxydecahydro-1, 4:5, 8-dimethanonaphthalene, and 2-ethyl-2-(meth)acryloyloxynorbornane. Commercially available products can be used as these monomers.

The iodine-containing (meth)acrylate (co)polymer represented by the general formula (5) obtained from the iodine-containing (meth)acrylate compound represented by the general formula (2), the iodine-containing (meth)acrylate (co)polymer represented by the general formula (6) obtained from the iodine-containing (meth)acrylate compound represented by the general formula (3), and the iodine-containing (meth)acrylate (co)polymer represented by the general formula (6') obtained from the iodine-containing (meth)acrylate compound represented by the general formula (3') can also be obtained by the same method. The iodine-containing (meth)acrylate (co)polymer represented by the general formula (5) or the general formula (6) is preferable for improving the performance of the material for film formation for lithography.

(5)

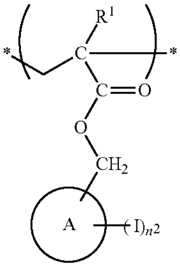

(In the formula (5), $R^1$, $n^2$, A, and symbol * are as defined in the formula (4).)

(6)

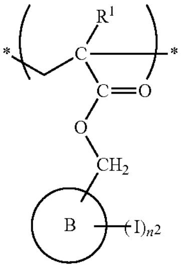

(In the formula (6),

B is as defined in the formula (3), and $R^1$, $n^2$, and symbol * are as defined in the formula (4).)

(6')

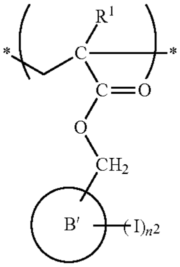

(In the formula (6'),

B' is as defined in the formula (3'), and $R^1$, $n^2$, and symbol * are as defined in the formula (4).)

Next, a method for producing an iodine-containing (meth) acrylate (co)polymer by polymerization reaction will be described. The polymerization reaction is carried out by dissolving a monomer to be a repeating unit in a solvent, adding a catalyst, and heating or cooling. The reaction conditions can be arbitrarily set depending on the kind of the initiator, the initiation method such as heat or light, the temperature, the pressure, the concentration, the solvent, the additive, and the like. The iodine-containing (meth)acrylate (co)polymer of the present invention can be produced by a publicly known method such as radical polymerization using a radical generating agent such as azoisobutyronitrile or peroxide, or ion polymerization using a catalyst such as alkyllithium or Grignard reagent.

As the solvent used in the polymerization reaction, commercially available products that are generally available can be used. For example, various solvents such as an alcohol, an ether, a hydrocarbon, and a halogen-based solvent can be arbitrarily used as long as the reaction is not inhibited. A mixture of a plurality of solvents may be used as long as the reaction is not inhibited.

The iodine-containing (meth)acrylate (co)polymer obtained by the polymerization reaction can be purified by a publicly known method. Specifically, ultrafiltration, crystallization, microfiltration, acid washing, washing with water having an electric conductivity of 10 mS/m or less and extraction can be carried out in combination.

[Composition Containing Iodine-Containing (Meth)Acrylate Compound and/or Iodine-Containing (Meth)Acrylate (Co)Polymer]

A composition of the present embodiment contains an iodine-containing (meth)acrylate compound and/or an iodine-containing (meth)acrylate (co)polymer, and is particularly suitable for lithography techniques. The composition can be used for, without particular limitation, film formation purposes for lithography, for example, resist film formation purposes (that is, a "resist composition"). Furthermore, the composition can be used for upper layer film formation purposes (that is, a "composition for upper layer film formation"), intermediate layer formation purposes (that is, a "composition for intermediate layer formation"), underlayer film formation purposes (that is, a "composition for underlayer film formation"), and the like. According to the composition of the present embodiment, not only a film having high sensitivity can be formed, but also the composition can also impart a good shape to a resist pattern.

The composition of the present embodiment can also be used as an optical component forming composition applying lithography technology. The optical component is used in the form of a film or a sheet and is also useful as a plastic lens (a prism lens, a lenticular lens, a microlens, a Fresnel lens, a viewing angle control lens, a contrast improving lens, etc.), a phase difference film, a film for electromagnetic wave shielding, a prism, an optical fiber, a solder resist for flexible printed wiring, a plating resist, an interlayer insulating film for multilayer printed circuit boards, a photosensitive optical waveguide, a liquid crystal display, an organic electroluminescent (EL) display, an optical semiconductor (LED) element, a solid state image sensing element, an organic thin film solar cell, a dye sensitized solar cell, and an organic thin film transistor (TFT). The composition can be particularly suitably utilized as an embedded film and a smoothed film on a photodiode, a smoothed film in front of or behind a color filter, a microlens, and a smoothed film and a conformal film on a microlens, all of which are components of a solid state image sensing element, to which high refractive index is demanded.

The composition of the present embodiment contains an iodine-containing (meth)acrylate compound and/or an iodine-containing (meth)acrylate (co)polymer (B), and may also contain other components such as a base material (A), a solvent (S), an acid generating agent (C), an acid diffusion controlling agent (E), and a base generating agent (G), if required. Hereinafter, each of these components will be described.

[Base material (A)]

The "base material (A)" in the present embodiment is a compound (including a resin) other than the iodine-containing (meth)acrylate compound and/or an iodine-containing (meth)acrylate (co)polymer, and means a base material applied as a resist for g-ray, i-ray, KrF excimer laser (248 nm), ArF excimer laser (193 nm), extreme ultraviolet (EUV) lithography (13.5 nm) or electron beam (EB) (for example, a base material for lithography or a base material for resist). These base materials can be used as the base material (A) according to the present embodiment without particular limitation. Examples of the base material (A) include a phenol novolac resin, a cresol novolac resin, a hydroxystyrene resin, a (meth)acrylic resin, a hydroxystyrene-(meth) acrylic copolymer, a cycloolefin-maleic anhydride copolymer, a cycloolefin, a vinyl ether-maleic anhydride copolymer, an inorganic resist material having a metallic element such as titanium, tin, hafnium and zirconium, and a derivative thereof. Among them, from the viewpoint of the shape of a resist pattern to be obtained, preferable are a phenol novolac resin, a cresol novolac resin, a hydroxystyrene resin, a (meth)acrylic resin, a hydroxystyrene-(meth) acrylic copolymer, an inorganic resist material having a metallic element such as titanium, tin, hafnium and zirconium, and a derivative thereof.

Examples of the above derivative include, but not particularly limited to, those to which a dissociation group is introduced and those to which a crosslinkable group is introduced. The above derivative to which a dissociation group or a crosslinkable group is introduced can exhibit dissociation reaction or crosslinking reaction through the effect of light, acid or the like.

The "dissociation group" refers to a characteristic group that is cleaved to generate a functional group such as an alkali soluble group that alters solubility. Examples of the alkali-soluble group include, but not particularly limited to, a phenolic hydroxy group, a carboxyl group, a sulfonic acid group, and a hexafluoroisopropanol group. A phenolic hydroxy group and a carboxyl group are preferable, and a phenolic hydroxy group is particularly preferable.

The "crosslinkable group" refers to a group that crosslinks in the presence of a catalyst or without a catalyst. Examples of the crosslinkable group include, but not particularly limited to, an alkoxy group having 1 to 20 carbon atoms, a group having an allyl group, a group having a (meth) acryloyl group, a group having an epoxy (meth)acryloyl group, a group having a hydroxy group, a group having a urethane (meth)acryloyl group, a group having a glycidyl group, and a group having a vinyl containing phenylmethyl group.

[Solvent (S)]

As a solvent according to the present embodiment, a publicly known solvent can be arbitrarily used as long as it can at least dissolve the iodine-containing (meth)acrylate compound and/or the iodine-containing (meth)acrylate (co) polymer mentioned above. Specific examples of the solvent can include, but not particularly limited to, an ethylene glycol monoalkyl ether acetate such as ethylene glycol monomethyl ether acetate, ethylene glycol monoethyl ether acetate, ethylene glycol mono-n-propyl ether acetate, and ethylene glycol mono-n-butyl ether acetate; an ethylene glycol monoalkyl ether such as ethylene glycol monomethyl ether and ethylene glycol monoethyl ether; a propylene glycol monoalkyl ether acetate such as propylene glycol monomethyl ether acetate (PGMEA), propylene glycol monoethyl ether acetate, propylene glycol mono-n-propyl ether acetate, and propylene glycol mono-n-butyl ether acetate; a propylene glycol monoalkyl ethers such as propylene glycol monomethyl ether (PGME) and propylene glycol monoethyl ether; a lactate ester such as methyl lactate, ethyl lactate, n-propyl lactate, n-butyl lactate, and n-amyl lactate; an aliphatic carboxylic acid ester such as methyl acetate, ethyl acetate, n-propyl acetate, n-butyl acetate, n-amyl acetate, n-hexyl acetate, methyl propionate, and ethyl propionate; another ester such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutyl acetate, 3-methyl-3-methoxybutyl acetate, butyl 3-methoxy-3-methylpropionate, butyl 3-methoxy-3-methylbutyrate, methyl acetoacetate, methyl pyruvate, and ethyl pyruvate; an aromatic hydrocarbon such as toluene and xylene; a ketone such as acetone, 2-butanone, 2-heptanone, 3-heptanone, 4-heptanone, cyclopentanone (CPN), and cyclohexanone (CHN); an amide such as N,N-dimethylformamide, N-methylacetamide, N,N-dimethylacetamide, and N-methylpyrrolidone; and a lactone such as γ-lactone. The solvent used in the present embodiment is preferably a safe solvent, more preferably at least one selected from PGMEA, PGME, CHN, CPN, 2-heptanone, anisole, butyl acetate and ethyl lactate, and still more preferably at least one selected from PGMEA, PGME, CHN, CPN and ethyl lactate.

In the present embodiment, the amount of the solid component and the amount of the solvent are not particularly limited, but preferably the solid component is 1 to 80% by mass and the solvent is 20 to 99% by mass, more preferably the solid component is 1 to 50% by mass and the solvent is 50 to 99% by mass, still more preferably the solid component is 2 to 40% by mass and the solvent is 60 to 98% by mass, and particularly preferably the solid component is 2 to 10% by mass and the solvent is 90 to 98% by mass, based on the total mass of the amount of the solid component and the solvent.

[Acid Generating Agent (C)]

The composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray and ion beam. The acid generating agent (C) is not particularly limited, and, for example, an acid generating agent described in International Publication No. WO 2013/024778 can be used. The acid generating agent (C) can be used alone or in combination of two or more kinds.

The amount of the acid generating agent (C) used is preferably 0.001 to 49% by mass of the total mass of the solid component, more preferably 1 to 40% by mass, still more preferably 3 to 30% by mass, and particularly preferably 10 to 25% by mass. By using the acid generating agent (C) within the above range, there is a tendency that a pattern profile with high sensitivity and low edge roughness is obtained. In the present embodiment, the acid generation method is not particularly limited as long as an acid is generated in the system. By using excimer laser instead of ultraviolet such as g-ray and i-ray, finer processing is possible, and also by using electron beam, extreme ultraviolet, X-ray or ion beam as a high energy ray, further finer processing is possible.

[Base Generating Agent (G)]

The case where the base generating agent (G) is a photobase generating agent will be described.

The photobase generating agent generates a base upon exposure and does not exhibit activity under normal conditions at normal temperature and pressure, but is not particularly limited as long as the photobase generating agent generates a base (basic substance) upon irradiation with an electromagnetic wave and heating as an external stimulus.

The photobase generating agent which can be used in the present invention is not particularly limited, and a publicly known one can be used, and examples thereof include, for example, a carbamate derivative, an amide derivative, an imide derivative, an α-cobalt complex, an imidazole derivative, a cinnamic acid amide derivative, and an oxime derivative.

The basic substance generated from the photobase generating agent is not particularly limited, and examples thereof include compounds having an amino group, particularly monoamines, polyamines such as diamines, and amidines.

The basic substance to be generated is preferably a compound having an amino group with a higher basicity (a higher pKa value of the conjugate acid) from the viewpoint of sensitivity and resolution.

Examples of the photobase generating agent include, for example, photobase generating agents having a cinnamic amide structure as disclosed in Japanese Patent Laid-Open No. 2009/80452 and International Publication NO. WO 2009/123122; base generating agents having a carbamate structure as disclosed in Japanese Patent Laid-Open No. 2006/189591 and Japanese Patent Laid-Open No. 2008/247747; base generating agents having an oxime structure or a carbamoyloxime structure as disclosed in Japanese Patent Laid-Open No. 2007/249013 and Japanese Patent Laid-Open No. 2008/003581; and compounds described in Japanese Patent Laid-Open No. 2010/243773, but these are not limited thereto, and other known structures of base generating agents can be used.

The photobase generating agent can be used alone or in combination of two or more kinds.

The preferred content of the photobase generating agent in actinic ray or radiation sensitive resin composition is similar to the preferred content of the aforementioned photoacid generating agent in actinic ray or radiation sensitive resin composition.

[Acid Diffusion Controlling Agent (E)]

In the present embodiment, the composition may contain an acid diffusion controlling agent (E) having a function of controlling diffusion of an acid generated from an acid generating agent by radiation irradiation in a resist film to inhibit any unpreferable chemical reaction in an unexposed region or the like. By using the acid diffusion controlling agent (E), there is a tendency that the storage stability of the composition of the present embodiment can be improved. Also, by using the acid diffusion controlling agent (E), there is a tendency that not only the resolution of a film formed by using the composition of the present embodiment can be improved, but the line width change of a resist pattern due to variation in the post exposure delay time before radiation irradiation and the post exposure delay time after radiation irradiation can also be inhibited, making the composition excellent in process stability. Examples of the acid diffusion controlling agent (E) include, but not particularly limited to, a radiation degradable basic compound such as a nitrogen atom containing basic compound, a basic sulfonium compound, and a basic iodonium compound.

The acid diffusion controlling agent (E) is not particularly limited, and, for example, an acid diffusion controlling agent described in International Publication No. WO 2013/024778 can be used. The acid diffusion controlling agent (E) can be used alone or in combination of two or more kinds.

The content of the acid diffusion controlling agent (E) is preferably 0.001 to 49% by mass of the total mass of the solid component, more preferably 0.01 to 10% by mass, still more preferably 0.01 to 5% by mass, and particularly preferably 0.01 to 3% by mass. When the content of the acid diffusion controlling agent (E) is within the above range, there is a tendency that a decrease in resolution, and deterioration of the pattern shape and the dimension fidelity or the like can be prevented. Moreover, even though the post exposure delay time from electron beam irradiation to heating after radiation irradiation becomes longer, the shape of the pattern upper layer portion can be prevented from being deteriorated. Also, when the content is 10% by mass or less, there is a tendency that a decrease in sensitivity, and developability of the unexposed portion or the like can be prevented. Also, by using such an acid diffusion controlling agent, there is a tendency that the storage stability of a resist composition is improved, also along with improvement of the resolution, the line width change of a resist pattern due to variation in the post exposure delay time before radiation irradiation and the post exposure delay time after radiation irradiation can be inhibited, making the composition excellent in process stability.

[Further Component (F)]

To the composition of the present embodiment, if required, as the further component (F), one kind or two kinds or more of various additive agents such as a crosslinking agent, a dissolution promoting agent, a dissolution controlling agent, a sensitizing agent, a surfactant, and an organic carboxylic acid or an oxo acid of phosphor or derivative thereof can be added.

(Crosslinking Agent)

In the present embodiment, one or more crosslinking agents can be contained in the composition. The crosslinking agent means a compound capable of crosslinking at least either a base material (A) or the iodine-containing (meth)acrylate compound and/or iodine-containing (meth)acrylate (co)polymer (B). It is preferable that the above crosslinking agent be an acid crosslinking agent capable of intramolecularly or intermolecularly crosslinking the base material (A) in the presence of the acid generated from the acid generating agent (C). Examples of such an acid crosslinking agent can include a compound having one or more groups capable of crosslinking the base material (A) (hereinafter, referred to as a "crosslinkable group").

Examples of the above crosslinkable group can include: (i) a hydroxyalkyl group or a group derived therefrom, such as a hydroxy (alkyl group having 1 to 6 carbon atoms), alkoxy having 1 to 6 carbon atoms (alkyl group having 1 to 6 carbon atoms) and acetoxy (alkyl group having 1 to 6 carbon atoms); (ii) a carbonyl group or a group derived therefrom, such as a formyl group and a carboxy (alkyl group having 1 to 6 carbon atoms); (iii) a nitrogenous group containing group such as a dimethylaminomethyl group, a diethylaminomethyl group, a dimethylolaminomethyl group, a diethylolaminomethyl group and a morpholinomethyl group; (iv) a glycidyl group containing group such as a glycidyl ether group, a glycidyl ester group and a glycidylamino group; (v) a group derived from an aromatic group such as an allyloxy having 1 to 6 carbon atoms (alkyl group having 1 to 6 carbon atoms) and an aralkyloxy having 1 to 6 carbon atoms (alkyl group having 1 to 6 carbon atoms) such as a benzyloxymethyl group and a benzoyloxymethyl group; and (vi) a polymerizable multiple bond containing group such as a vinyl group and an isopropenyl group. As the crosslinkable group of the crosslinking agent according to the present embodiment, a hydroxyalkyl group, an alkoxyalkyl group and the like are preferable, and an alkoxymethyl group is particularly preferable.

The crosslinking agent having the above crosslinkable group is not particularly limited, and, for example, an acid crosslinking agent described in International Publication No. WO 2013/024778 can be used. The crosslinking agent can be used alone or in combination of two or more kinds.

In the present embodiment, the content of the crosslinking agent is preferably 50% by mass or less of the total mass of the solid component, more preferably 40% by mass or less, still more preferably 30% by mass or less, and particularly preferably 20% by mass or less.

(Dissolution Promoting Agent)

The dissolution promoting agent is a component having a function of, when the solubility of a solid component is too low, increasing the solubility of the solid component in a developing solution to moderately increase the dissolution rate of that compound upon developing. As the above dissolution promoting agent, those having a low molecular weight are preferable, and examples thereof can include a phenolic compound having a low molecular weight. Examples of the phenolic compound having a low molecular weight can include a bisphenol and a tris(hydroxyphenyl) methane. These dissolution promoting agents can be used alone or in mixture of two or more kinds.

The content of the dissolution promoting agent, which is arbitrarily adjusted according to the kind of the above solid component to be used, is preferably 0 to 49% by mass of the total mass of the solid component, more preferably 0 to 5% by mass, still more preferably 0 to 1% by mass, and particularly preferably 0% by mass.

(Dissolution Controlling Agent)

The dissolution controlling agent is a component having a function of, when the solubility of a solid component is too high, controlling the solubility of the solid component in a developing solution to moderately decrease the dissolution rate upon developing. As such a dissolution controlling agent, the one which does not chemically change in steps such as calcination of resist coating, radiation irradiation, and development is preferable.

The dissolution controlling agent is not particularly limited, and examples thereof can include an aromatic hydrocarbon such as phenanthrene, anthracene and acenaphthene; a ketone such as acetophenone, benzophenone and phenyl naphthyl ketone; and a sulfone such as methyl phenyl sulfone, diphenyl sulfone and dinaphthyl sulfone. These dissolution controlling agents can be used alone or in combination of two or more kinds.

The content of the dissolution controlling agent, which is arbitrarily adjusted according to the kind of the above compound to be used, is preferably 0 to 49% by mass of the total mass of the solid component, more preferably 0 to 5% by mass, still more preferably 0 to 1% by mass, and particularly preferably 0% by mass.

(Sensitizing Agent)

The sensitizing agent is a component having a function of absorbing irradiated radiation energy, transmitting the energy to the acid generating agent (C), and thereby increasing the acid production amount, and improving the apparent sensitivity of a resist. Examples of such a sensitizing agent can include, but not particularly limited to, a benzophenone, a biacetyl, a pyrene, a phenothiazine and a fluorene. These sensitizing agents can be used alone or in combination of two or more kinds.

The content of the sensitizing agent, which is arbitrarily adjusted according to the kind of the above compound to be used, is preferably 0 to 49% by mass of the total mass of the solid component, more preferably 0 to 5% by mass, still more preferably 0 to 1% by mass, and particularly preferably 0% by mass.

(Surfactant)

The surfactant is a component having a function of improving coatability and striation of the composition of the present embodiment, and developability of a resist or the like. The surfactant may be any of anionic, cationic, nonionic, and amphoteric surfactants. Preferable examples of the surfactant include a nonionic surfactant. The nonionic surfactant has a good affinity with a solvent to be used in production of the composition of the present embodiment, and can further enhance the effects of the composition of the present embodiment. Examples of the nonionic surfactant include, but not particularly limited to, a polyoxyethylene higher alkyl ether, a polyoxyethylene higher alkyl phenyl ether, and a higher fatty acid diester of polyethylene glycol. Examples of commercially available products of these surfactants can include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.).

The content of the surfactant, which is arbitrarily adjusted according to the kind of the above solid component to be used, is preferably 0 to 49% by mass of the total mass of the solid component, more preferably 0 to 5% by mass, still more preferably 0 to 1% by mass, and particularly preferably 0% by mass.

(Organic Carboxylic Acid or Oxo Acid of Phosphor or Derivative Thereof)

For the purpose of prevention of sensitivity deterioration or improvement of a resist pattern shape and post exposure delay stability or the like, and as an additional optional component, the composition of the present embodiment can contain an organic carboxylic acid or an oxo acid of phosphor or derivative thereof. The organic carboxylic acid or the oxo acid of phosphor or derivative thereof can be used in combination with the acid diffusion controlling agent, or may be used alone. Suitable examples of the organic carboxylic acid include malonic acid, citric acid, malic acid, succinic acid, benzoic acid and salicylic acid. Examples of the oxo acid of phosphor or derivative thereof include phosphoric acid or derivative thereof such as ester including phosphoric acid, di-n-butyl phosphate and diphenyl phosphate; phosphonic acid or derivative thereof such as ester including phosphonic acid, dimethyl phosphonate, di-n-butyl phosphonate, phenylphosphonic acid, diphenyl phosphonate and dibenzyl phosphonate; and phosphinic acid and derivative thereof such as ester including phosphinic acid and phenylphosphinic acid. Among them, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the above compound to be used, is preferably 0 to 49% by mass of the total mass of the solid component, more preferably 0 to 5% by mass, still more preferably 0 to 1% by mass, and particularly preferably 0% by mass.

[Further Additive Agent]

Furthermore, the composition of the present embodiment can contain one kind or two kinds or more of additive agents other than the components mentioned above, if required. Examples of such an additive agent include a dye, a pigment and an adhesion aid. For example, when the composition contains a dye or a pigment, a latent image of the exposed portion is visualized and influence of halation upon exposure can be alleviated, which is preferable. Also, when the composition contains an adhesion aid, adhesiveness to a substrate can be improved, which is preferable. Furthermore, examples of the further additive agent can include a halation preventing agent, a storage stabilizing agent, a defoaming agent and a shape improving agent. Specific examples thereof can include 4-hydroxy-4'-methylchalkone.

In the composition of the present embodiment, the total content of the optional component (F) can be 0 to 99% by mass of the total mass of the solid component, and is preferably 0 to 49% by mass, more preferably 0 to 10% by mass, still more preferably 0 to 5% by mass, further preferably 0 to 1% by mass, and particularly preferably 0% by mass.

In order to form a resist pattern from the composition of the present invention, the composition solution is applied to a substrate such as a silicon wafer, a metal, a plastic, a glass or a ceramic by an appropriate application means such as a spin coater, a dip coater or a roller coater to form a resist film, and in some cases, heat treatment is carried out at a temperature of about 50° C. to 200° C. before exposure through a predetermined mask pattern. The thickness of the coating film is, for example, about 0.1 to 20 μm, preferably about 0.3 to 2 μm. For exposure, rays of various wavelengths such as ultraviolet rays and X-rays can be used, and for example, far ultraviolet rays such as F2 excimer laser (wavelength: 157 nm), ArF excimer laser (wavelength: 193 nm) and KrF excimer laser (wavelength: 248 nm), extreme ultraviolet rays (wavelength: 13 nm), X-rays, and electron beams can be arbitrarily selected and used as light sources. The exposure conditions such as the amount of exposure are arbitrarily selected in accordance with the compounding composition of the resin and/or the compound and the type of each additive.

In the present invention, in order to stably form a fine pattern with a high degree of accuracy, it is preferable to perform a heat treatment at a temperature of 50 to 200° C. for 30 seconds or longer after exposure. In this case, when the temperature is less than 50° C., variations in the sensitivity is likely to spread depending on the type of the substrate. Thereafter, a predetermined resist pattern is formed by developing with an alkaline developer, typically at 10 to 50° C. for 10 to 200 seconds, and preferably at 20 to 25° C. for 15 to 90 seconds.

As the alkaline developer, for example, an alkaline aqueous solution obtained by dissolving an alkaline compound such as an alkali metal hydroxide, an aqueous ammonia, an alkylamine, an alkanolamine, a heterocyclic amine, a tetraalkylammonium hydroxide, choline, 1,8-diazabicyclo-[5.4.0]-7-undecene, 1,5-diazabicyclo-[4.3.0]-5-nonene at a concentration of 1 to 10% by weight, preferably 1 to 3% by weight, is used. Further, a water-soluble organic solvent or a surfactant may be appropriately added to the developer comprising the alkaline aqueous solution.

In the present embodiment, in order to stably form a fine pattern with a high degree of accuracy, it is also possible to form a resist pattern by performing a developing process with a developer containing an organic solvent as a main component after exposure and PEB.

As the organic solvent used for the developer, various organic solvents are widely used, and for example, solvents such as an ester-based solvent, a ketone-based solvent, an alcohol-based solvent, an amide-based solvent, an ether-based solvent, and a hydrocarbon-based solvent can be used.

The developer preferably contains at least one kind of solvent selected from a ketone-based solvent, an ester-based solvent, an alcohol-based solvent and an ether-based solvent.

Examples of the ester-based solvent include, for example, methyl acetate, ethyl acetate, butyl acetate, isobutyl acetate, pentyl acetate, propyl acetate, isopropyl acetate, amyl acetate (pentyl acetate), isoamyl acetate (isopentyl acetate, 3-methylbutyl acetate), 2-methylbutyl acetate, 1-methylbutyl acetate, hexyl acetate, isohexyl acetate, heptyl acetate, octyl acetate, ethyl methoxy acetate, ethyl ethoxy acetate, propylene glycol monomethyl ether acetate (PGMEA; otherwise known as 1-methoxy-2-acetoxypropane), ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monopropyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3 methoxypentyl acetate, 3-methyl-4-methoxypentyl acetate, 4-methyl-4 methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, butyl propionate, isobutyl propionate, pentyl propionate, hexyl propionate, heptyl propionate, butyl butanoate, isobutyl butanoate, pentyl butanoate, hexyl butanoate, isobutyl isobutanoate, propyl pentanoate, isopropyl pentanoate, butyl pentanoate, pentyl pentanoate, ethyl hexanoate, propyl hexanoate, butyl hexanoate, isobutyl hexanoate, methyl heptanoate, ethyl heptanoate, propyl heptanoate, cyclohexyl acetate, cycloheptyl acetate, 2-ethylhexyl acetate, cyclopentyl propionate, methyl 2-hydroxypropionate, ethyl 2-hydroxypropionate, methyl-3-methoxypropionate, ethyl-3-methoxypropionate, ethyl-3-ethoxypropionate, and propyl-3-ethoxypropionate. Among these, butyl acetate, amyl acetate, isoamyl acetate, 2-methylbutyl acetate, 1-methylbutyl acetate, hexyl acetate, pentyl propionate, hexyl propionate, heptyl propionate, methyl hydroxyisobutyrate, or butyl butanoate is preferably used, and butyl acetate, isoamyl acetate, and methyl hydroxyisobutyrate are particularly preferably used.

Examples of the ketone-based solvent can include, for example, 1-octanone, 2-octanone, 1-nonanone, 2-nonanone, acetone, 2-heptanone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, propylene carbonate, and γ-butyrolactone. Among them, 2-heptanone is preferred.

Examples of the alcohol-based solvent include, for example, alcohols such as methanol, ethanol, 1-propanol, isopropanol, 1-butanol, 2-butanol, 3-methyl-1-butanol, tert-butyl alcohol, 1-pentanol, 2-pentanol, 1-hexanol, 1-heptanol, 1-octanol, 1-decanol, 2-hexanol, 2-heptanol, 2-octanol, 3-hexanol, 3-heptanol, 3-octanol, 4-octanol, 3-methyl-3-pentanol, cyclopentanol, 2,3-dimethyl-2-butanol, 3,3-dimethyl-2-butanol, 2-methyl-2-pentanol, 2-methyl-3-pentanol, 3-methyl-2-pentanol, 3-methyl-3-pentanol, 4-methyl-2-pentanol, 4-methyl-3-pentanol, cyclohexanol, 5-methyl-2-hexanol, 4-methyl-2-hexanol, 4,5-dithyl-2hexal, 6-methyl-2-heptanol, 7-methyl-2-octanol, 8-methyl-2-nonal, 9-methyl-2-decanol, and 3-methoxy-1-butanol (monohydric alcohol); glycol-based solvents such as ethylene glycol, diethylene glycol, and triethylene glycol; glycol ether-based solvents containing hydroxy groups such as ethylene glycol monomethyl ether, propylene glycol monomethyl ether (PGME; otherwise known as l-methoxy-2-propanol), diethylene glycol monomethyl ether, triethylene glycol monoethyl ether, methoxymethyl butanol, ethylene glycol monoethyl ether, ethylene glycol monopropyl ether, ethylene glycol monobutyl ether, propylene glycol monoethyl ether, propylene glycol monopropyl ether, propylene glycol monobutyl ether, and propylene glycol monophenyl ether; and the like. Among these, a glycol ether solvent is preferably used.

Examples of the ether-based solvent include, for example, in addition to the glycol ether-based solvent containing hydroxy groups, glycol ether-based solvents not containing hydroxy groups such as propylene glycol dimethyl ether, propylene glycol diethyl ether, diethylene glycol dimethyl ether, and diethylene glycol diethyl ether; aromatic ether solvents such as anisole and phenetol; dioxane, tetrahydrofuran, tetrahydropyran, perfluoro-2-butyltetrahydrofuran, perfluorotetrahydrofuran, 1,4-dioxane, and isopropyl ether. Among them, glycol ether-based solvents and aromatic ether solvents such as anisole are preferable.

Examples of the amide-based solvent include N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon solvent include aliphatic hydrocarbon solvents such as pentane, hexane, octane, nonane, decane, dodecane, undecane, hexadecane, 2,2,4-trimethylpentane, 2,2,3-trimethylhexane, perfluorohexane, and perfluoroheptane; and aromatic hydrocarbon solvents such as toluene, xylene, ethylbenzene, propylbenzene, 1-methylpropylbenzene, 2-methylpropylbenzene, dimethylbenzene, diethylbenzene, ethylmethylbenzene, trimethylbenzene, ethyldimethylbenzene, and dipropylbenzene.

As the hydrocarbon-based solvent, an unsaturated hydrocarbon-based solvent can also be used, and examples thereof include unsaturated hydrocarbon-based solvents such as octene, nonene, decene, undecene, dodecene, and hexadecene. The number of double bonds or triple bonds of the unsaturated hydrocarbon solvent is not particularly limited, and the unsaturated hydrocarbon solvent may have a double bond or a triple bond at any position of the hydrocarbon chain. When the unsaturated hydrocarbon solvent has a double bond, a cis isomer and a trans isomer may be mixed.

The aliphatic hydrocarbon-based solvent which is a hydrocarbon-based solvent may be a mixture of compounds having the same carbon number but different structures. For example, when decane is used as the aliphatic hydrocarbon-based solvent, 2-methylnonane, 2,2-dimethyloctane, 4-ethyloctane, isooctane and the like which are compounds having the same number of carbon atoms and different structures may be contained in the aliphatic hydrocarbon-based solvent.

Further, only one kind of compounds having the same carbon number and different structures may be contained, or a plurality of kinds may be contained as described above.

Further, a basic compound, a water-soluble organic solvent or a surfactant may be appropriately added to the developer comprising the organic solvent.

EXAMPLES

Hereinafter, the present invention will be described in further detail with reference to Examples and Comparative Examples, but the present invention is not limited by these examples in any way.

[Measurement Method]

(1) Structure of Compound

The structure of the compound was verified by carrying out $^1$H-NMR measurement under the following conditions using a product from Bruker, "Advance 600 II spectrometer".

Frequency: 400 MHz

Solvent: $CDCl_3$ or $d_6$-DMSO

Internal standard: TMS

Measurement temperature: 23° C.

(Synthesis Example 1-1) Synthesis of MAC-4I

Into 200 ml of methanol, 23 g (0.1 mol) of 4-iodobenzaldehyde was dissolved, and 9.5 g (0.25 mol) of $NaBH_4$ was added thereto at 10° C. or lower. Subsequently, the mixture was stirred and reacted for 3 hours, and methanol was distilled off under reduced pressure and concentrated. Water and ethyl acetate were added to the concentrate, and the organic phase was extracted. The organic phase was dried over sodium sulfate added, and the solvent was distilled off under reduced pressure to obtain a crude product of 4-iodobenzyl alcohol. The obtained crude product of 4-iodobenzyl alcohol was purified by column chromatography to obtain 22 g (yield: 94%) of 4-iodobenzyl alcohol shown below.

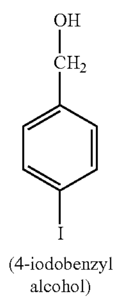

(4-iodobenzyl alcohol)

In chloroform, 11.5 g (50 mmol) of 4-iodobenzyl alcohol obtained above was dissolved, 4.4 g (55 mmol) of pyridine was added under ice-cooling, and 5.7 g (55 mmol) of methacrylic acid chloride was dropwise thereto. Subsequently, the mixture was stirred and reacted under ice-cooling for 1 hour and at room temperature for 3 hours. After completion of the reaction, water was added to the reaction liquid, and the mixture was washed with saturated aqueous sodium hydrogen carbonate solution. The organic phase was dried over sodium sulfate, concentrated, and purified by column chromatography to obtain 13 g (yield: 88%) of the objective product MAC-4I shown below.

When the obtained compound (MAC-4I) was subjected to NMR measurement under the above measurement conditions, the following peaks were found, and it was confirmed that the compound had a chemical structure represented by the formula (MAC-4I):

δ (ppm) ($CDCl_3$): 7.7 (2H, Ph), 7.1 (2H, Ph), 6.1 (1H, $=CH_2$), 5.6 (1H, $=CH_2$), 5.1 (2H), 2.0 (3H, $-CH_3$)

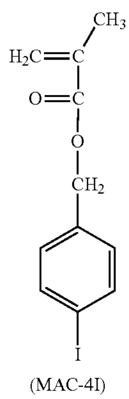

(MAC-4I)

(Synthesis Example 2-1) Synthesis of MAC-2H35I

Into 900 ml of methanol, 90 g (0.24 mol) of 3,5-diiodosalicylaldehyde was dissolved, and 22.8 g (0.60 mol) of $NaBH_4$ was added thereto at 10° C. or lower. Subsequently, the mixture was stirred and reacted under ice-cooling for 3 hours, then stirred at 25° C. for 16 hours to react, and methanol was distilled off under reduced pressure and concentrated. Water and ethyl acetate were added to the concentrate, and the organic phase was extracted. The organic phase was dried over magnesium sulfate added, and the solvent was distilled off under reduced pressure to obtain a crude product of 2-hydroxy-3,5-diiodobenzyl alcohol. The obtained crude product of 2-hydroxy-3,5-diiodobenzyl alcohol was purified by column chromatography to obtain 82.5 g (91% yield) of 2-hydroxy-3,5-diiodobenzyl alcohol shown below.

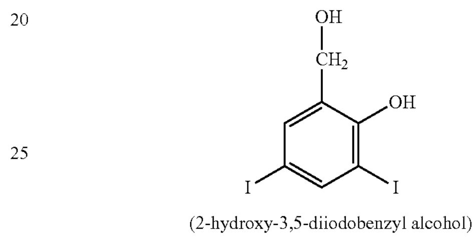

(2-hydroxy-3,5-diiodobenzyl alcohol)

In 100 mL of dichloromethane, 10 g (27 mmol) of 2-hydroxy-3,5-diiodobenzyl alcohol obtained above was dissolved, 3.1 g (39 mmol) of pyridine was added under ice-cooling, and 4.1 g (27 mmol) of methacrylic anhydride was dropwise thereto. Subsequently, the mixture was stirred and reacted under ice-cooling for 4 hours and at room temperature for 18 hours. After completion of the reaction, water was added to the reaction liquid, and the mixture was washed with aqueous sodium hydrogen carbonate solution. The organic phase was dried over magnesium sulfate, concentrated, and purified by column chromatography to obtain 9 g (yield: 88%) of the objective product MAC-2H35I shown below.

When the obtained compound (MAC-2H35I) was subjected to NMR measurement under the above measurement conditions, the following peaks were found, and it was confirmed that the compound had a chemical structure represented by the formula (MAC-2H35I):

δ (ppm) ($CDCl_3$): 7.2-8.0 (2H, Ph), 7.6 (1H, —OH), 6.2 (1H, $=CH_2$), 5.7 (1H, $=CH_2$), 5.1 (2H, $-CH_2-$), 2.0 (3H, $-CH_3$)

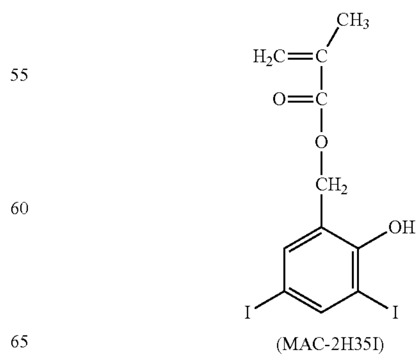

(MAC-2H35I)

(Synthesis Example 3-1) Synthesis of MAC-4H35I

In 2.8 L of ethanol, 128 g (0.78 mol) of calcium chloride and 91.3 g (2.4 mol) of $NaBH_4$ were dissolved, and 410 g (1.1 mol) of 4-hydroxy-3,5-diiodobenzaldehyde was added thereto under ice-cooling. After the reaction was carried out by stirring at 25° C. for 18 hours, 10 L of water was added to the mixture, the pH was adjusted to 2.5 with hydrochloric acid, and the precipitate was filtered, washed with water, and dried to obtain 401 g (97%: yield) of 4-hydroxy-3,5-diiodobenzyl alcohol shown below.

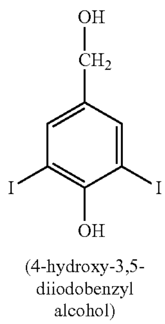 [SMILES: OCc1cc(I)c(O)c(I)c1]

(4-hydroxy-3,5-diiodobenzyl alcohol)

In 2.8 L of toluene, 400 g (1.06 mol) of 4-hydroxy-3,5-diiodobenzyl alcohol obtained above was dissolved, and 916 g (10.6 mol) of methacrylic acid, 20 g of paratoluenesulfonic acid monohydrate (0.105 mol), and 13 mg (0.01 mmol) of 4-methoxyphenol were added thereto, followed by stirring at 110° C. under reflux for 2 hours. After the reaction, 4 L of water was added to the reaction mixture to dry the organic layer, and the organic layer was purified by recrystallization twice with hexane to obtain 158 g (yield: 33%) of the objective product MAC-4H35I shown below.

When the obtained compound (MAC-4H35I) was subjected to NMR measurement under the above measurement conditions, the following peaks were found, and it was confirmed that the compound had a chemical structure represented by the formula (MAC-4H35I):

δ (ppm) ($CDCl_3$): 9.7 (1H, —OH), 7.8 (2H, Ph), 6.7 (1H, $=CH_2$), 5.0 (1H, $=CH_2$), 5.0 (2H, $—CH_2—$), 1.9 (3H, $—CH_3$)

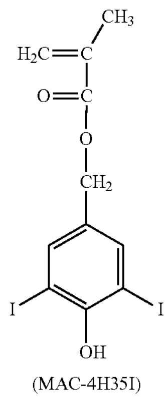

(MAC-4H35I)

(Synthesis Example 3-2) Synthesis of MAC-4H35I

In 600 mL of methanol, 45.0 g (0.36 mol) of 4-hydroxybenzyl alcohol and 92.4 g (0.36 mol) of iodine were dissolved, and 6.2 g (0.18 mol) of hydrogen peroxide was added dropwise thereto in a 20° C. water bath, followed by stirring at 80° C. for 8 hours to cause reaction. After cooling, the mixture was washed by separation treatment using an aqueous sodium thiosulfate solution and brine, and then the organic phase was extracted. The organic phase was dried over magnesium sulfate added, and the solvent was distilled off under reduced pressure to obtain a crude product of 4-hydroxy-3,5-diiodobenzyl alcohol. The obtained crude product of 4-hydroxy-3,5-diiodobenzyl alcohol was purified by column chromatography to obtain 95 g (70% yield) of 4-hydroxy-3,5-diiodobenzyl alcohol.

Using the 4-hydroxy-3,5-diiodobenzyl alcohol obtained above, MAC-4H35I was obtained in the same manner as in Synthesis Example 3-1.

(Synthesis Example 4-1) Synthesis of MAC-2H35I-BOC

In a container (internal capacity: 200 mL) equipped with a stirrer, a condenser tube, and a burette, 5.5 g (12.4 mmol) of the compound (MAC-2H35I) obtained in Synthesis Example 2-1, and 2.7 g (12.4 mmol) of di-t-butyl dicarbonate (manufactured by Sigma-Aldrich) were fed to 100 mL of acetone, 1.71 g (12.4 mmol) of potassium carbonate (manufactured by Sigma-Aldrich) was added, and the contents were reacted by being stirred at 20° C. for 6 hours to obtain a reaction liquid. Next, the reaction liquid was concentrated, and the reaction product was precipitated by the addition of 100 g of pure water to the concentrate, cooled to room temperature, and then filtered to separate solid matter.

The obtained solid matter was filtered, dried, and then separated and purified by column chromatography, thereby obtaining 1.5 g of the objective compound (MAC-2H35I-BOC) represented by the following formula (MAC-2H35I-BOC).

When the obtained compound (MAC-2H35I-BOC) was subjected to NMR measurement under the above measurement conditions, the following peaks were found, and it was confirmed that the compound had a chemical structure represented by the formula (MAC-2H35I-BOC):

δ (ppm) ($CDCl_3$): 7.2-8.0 (2H, Ph), 6.2 (1H, $=CH_2$), 5.7 (1H, $=CH_2$), 5.1 (2H, $—CH_2—$), 2.0 (3H, $—CH_3$), 1.4 (9H, $—CH_3)_3$)

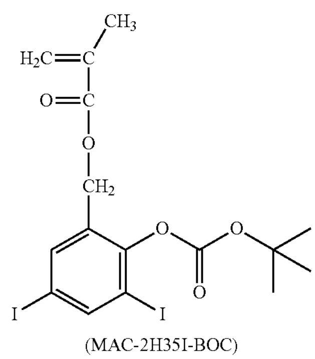

(MAC-2H35I-BOC)

(Synthesis Example 5-1) Synthesis of MAC-2H35I-MeBOC

In a container (internal capacity: 200 mL) equipped with a stirrer, a condenser tube, and a burette, 5.5 g (12.4 mmol)

of the compound (MAC-2H35I) obtained in Synthesis Example 2-1 and 2.42 g (12.4 mmol) of t-butyl bromoacetate (manufactured by Sigma-Aldrich) were fed to 100 mL of acetone, 1.71 g (12.4 mmol) of potassium carbonate (manufactured by Sigma-Aldrich) and 0.4 g of 18-crown-6 were added, and the contents were reacted by being stirred under reflux for 3 hours to obtain a reaction liquid. Next, the reaction liquid was concentrated, and the reaction product was precipitated by the addition of 100 g of pure water to the concentrate, cooled to room temperature, and then filtered to separate solid matter.

The obtained solid matter was filtered, dried, and then separated and purified by column chromatography, thereby obtaining 1.4 g of the objective compound (MAC-2H35I-MeBOC) represented by the following formula (MAC-2H35I-MeBOC).

When the obtained compound (MAC-2H35I-MeBOC) was subjected to NMR measurement under the above measurement conditions, the following peaks were found, and it was confirmed that the compound had a chemical structure represented by the formula (MAC-2H35I-MeBOC):

δ (ppm) ($CDCl_3$): 7.8 (2H, Ph), 6.7 (1H, $=CH_2$), 5.7 (1H, $=CH_2$), 5.0 (4H, O—$CH_2$-Ph, O—$CH_2$-0), 1.9 (3H, —$CH_3$), 1.4 (9H, —$(CH_3)_3$)

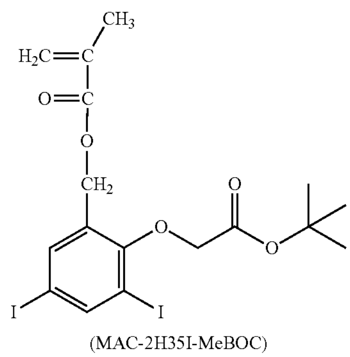

(MAC-2H35I-MeBOC)

(Synthesis Example 6-1) Synthesis of MAC-4H35I-BOC

In the same manner as in Synthesis Example 4-1 except that the compound (MAC-4H35I) was used instead of the compound (MAC-2H35I), 1.5 g of an objective compound (MAC-4H35I-BOC) represented by the following formula (MAC-4H35I-BOC) was obtained.

When the obtained compound (MAC-4H35I-BOC) was subjected to NMR measurement under the above measurement conditions, the following peaks were found, and it was confirmed that the compound had a chemical structure represented by the formula (MAC-4H35I-BOC):

δ (ppm) ($CDCl_3$): 7.8 (2H, Ph), 6.2 (1H, $=CH_2$), 5.7 (1H, $=CH_2$), 5.1 (2H, —$CH_2$—), 2.0 (3H, —$CH_3$), 1.4 (9H, —$CH_3)_3$)

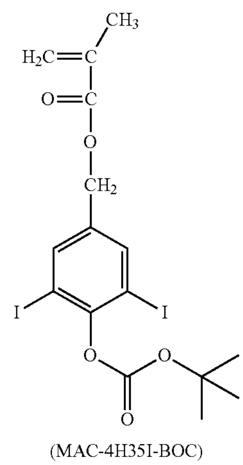 [SMILES: C=C(C)C(=O)OCc1cc(I)c(OC(=O)OC(C)(C)C)c(I)c1 ; "(MAC-4H35I-BOC)"]

(MAC-4H35I-BOC)

(Synthesis Example 7-1) Synthesis of MAC-4H35I-MeBOC

In the same manner as in Synthesis Example 5-1 except that the compound (MAC-4H35I) was used instead of the compound (MAC-2H35I), 1.5 g of an objective compound (MAC-4H35I-MeBOC) represented by the following formula (MAC-4H35I-MeBOC) was obtained.

When the obtained compound (MAC-4H35I-MeBOC) was subjected to NMR measurement under the above measurement conditions, the following peaks were found, and it was confirmed that the compound had a chemical structure represented by the formula (MAC-4H35I-MeBOC):

δ (ppm) ($CDCl_3$): 7.8 (2H, Ph), 6.8 (2H, O—$CH_2$-0), 6.7 (1H, $=CH_2$), 5.7 (1H, $=CH_2$), 5.1 (2H, O—$CH_2$-Ph), 2.0 (2H, —$CH_3$), 1.4 (9H, —$(CH_3)_3$))

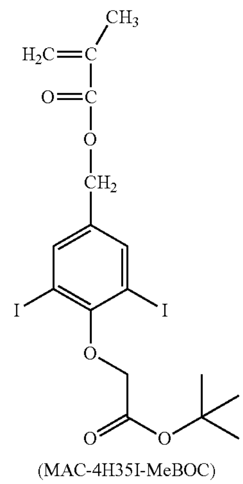

(MAC-4H35I-MeBOC)

(Synthesis Example 8-1) Synthesis of ACLAC-2H35I

In a 300 mL eggplant flask equipped with a Dean Stark and reflux tube, 10.2 g (27 mmol) of 2-hydroxy-3,5-diiodobenzyl alcohol obtained in (Synthesis Example 2-1) was dissolved in 100 mL of toluene, 0.05 g (0.3 mmol) of p-toluene sulfonic acid was added under ice-cooling, and 2.9 g (27 mmol) of α-chloroacrylate was added dropwise thereto. Subsequently, the mixture was stirred and reacted under reflux conditions for 1 hour. After completion of the reaction, water was added to the reaction liquid, and the mixture was washed with aqueous sodium hydrogen carbonate solution. The organic phase was dried over magnesium sulfate, concentrated, and purified by column chromatography to obtain 9.3 g (yield: 73%) of the objective product ACLAC-2H35I shown below.

When the obtained compound (ACLAC-2H35I) was subjected to NMR measurement under the above measurement conditions, the following peaks were found, and it was confirmed that the compound had a chemical structure represented by the formula (ACLAC-2H35I):

δ (ppm) ($CDCl_3$): 7.2-8.0 (2H, Ph), 9.6 (1H, —OH), 6.0 (1H, $=CH_2$), 6.6 (1H, $=CH_2$), 5.1 (2H, $—CH_2—$)

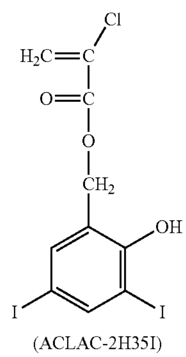

(ACLAC-2H35I)

(Synthesis Example 9-1) Synthesis of MAC-ADI

In 200 mL of toluene, 16.8 g (0.1 mol) of 1,3-adamantanediol (manufactured by Mitsubishi Gas Chemical) was added with 89.8 g (0.4 mol) of a 57% aqueous solution of hydrogen iodide, and the mixture was stirred at 80° C. for 8 hours to react. After the reaction, water was added, washing was performed with sodium hydrogen carbonate, and the organic layer was concentrated and then separated and purified by column chromatography to obtain 12 g of 3-iodo-1-hydroxyadamantane represented by the following formula.

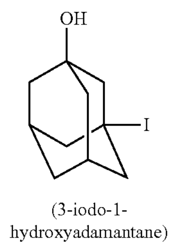 [SMILES: OC12CC3CC(C1)CC(I)(C3)C2]

(3-iodo-1-hydroxyadamantane)

In chloroform, 2.78 g (10 mmol) of 3-iodo-1-hydroxyadamantane obtained above was dissolved, 0.96 g (12 mmol) of pyridine was added under ice-cooling, and 1.25 g (12 mmol) of methacrylic acid chloride was dropwise thereto. Subsequently, the mixture was stirred and reacted under ice-cooling for 1 hour and at room temperature for 3 hours. After completion of the reaction, water was added to the reaction liquid, and the mixture was washed with saturated aqueous sodium hydrogen carbonate solution. The organic phase was dried over sodium sulfate, concentrated, and purified by column chromatography to obtain 2.7 g of the objective product (MAC-ADI) shown below.

When the obtained compound (MAC-ADI) was subjected to NMR measurement under the above measurement conditions, the following peaks were found, and it was confirmed that the compound had a chemical structure represented by the formula (MAC-ADI):

δ (ppm) (d-DMSO): 6.4-6.5 (2H, =CH2), 1.3-3.2 (17H, Ad-H, —C(CH3)=C)

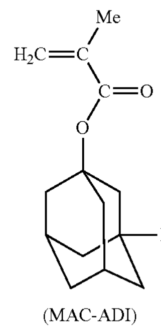

(MAC-ADI)

(Synthesis Example 10-1) Synthesis of MAC-ADI2

In 100 mL of toluene, 2.3 g (12.5 mmol) of 1,3,5-adamantanetriol (manufactured by Mitsubishi Gas Chemical) was added with 28.1 g (125 mmol) of a 57% aqueous solution of hydrogen iodide, and the mixture was stirred at 80° C. for 13 hours to react. After the reaction, water was added, washing was performed with sodium hydrogen carbonate, and the organic layer was concentrated and then separated and purified by column chromatography to obtain 0.9 g of 3,5-diiodo-1-hydroxyadamantane represented by the following formula.

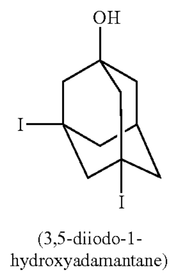 [SMILES: OC12CC3CC(I)(C1)CC(I)(C3)C2]

(3,5-diiodo-1-hydroxyadamantane)

In the same manner as in Synthesis Example 9-1 except that 4.04 g (10 mmol) of 3,5-diiodo-1-hydroxyadamantane obtained above was used instead of 2.78 g of 3-iodo-1-hydroxyadamantane, 3.5 g of an objective compound (MAC-ADI2) represented by the following formula (MAC-ADI2) was obtained.

When the obtained compound (MAC-ADI2) was subjected to NMR measurement under the above measurement conditions, the following peaks were found, and it was confirmed that the compound had a chemical structure represented by the formula (MAC-ADI2):

δ (ppm) (d-DMSO): 6.4-6.5 (2H, =CH2), 1.5-3.9 (16H, Ad-H, —C(CH3)=C)

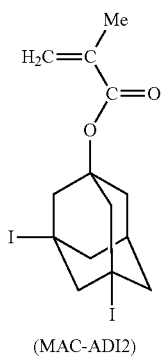

(MAC-ADI2)

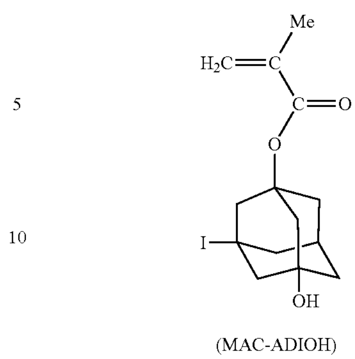

(MAC-ADIOH)

(Synthesis Example 11-1) Synthesis of MAC-ADIOH

In 100 mL of toluene, 2.3 g (12.5 mmol) of 1,3,5-adamantanetriol (manufactured by Mitsubishi Gas Chemical) was added with 28.1 g (125 mmol) of a 57% aqueous solution of hydrogen iodide, and the mixture was stirred at 80° C. for 13 hours to react. After the reaction, water was added, washing was performed with sodium hydrogen carbonate, and the organic layer was concentrated and then separated and purified by column chromatography to obtain 0.9 g of 5-iodo-1,5-dihydroxyadamantane represented by the following formula.

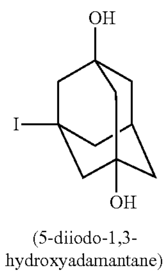 [SMILES: OC12CC3CC(O)(C1)CC(I)(C3)C2]

(5-diiodo-1,3-hydroxyadamantane)

In the same manner as in Synthesis Example 9-1 except that 4.04 g (10 mmol) of 5-iodo-1,3-dihydroxyadamantane obtained above was used instead of 2.78 g of 3-iodo-1-hydroxyadamantane, 3.5 g of an objective compound (MAC-ADIOH) represented by the following formula (MAC-ADIOH) was obtained.

When the obtained compound (MAC-ADIOH) was subjected to NMR measurement under the above measurement conditions, the following peaks were found, and it was confirmed that the compound had a chemical structure represented by the formula (MAC-ADIOH):

δ (ppm) (d-DMSO): 6.4-6.5 (2H, =CH2), 1.5-3.9 (14H, Ad-H, —C(CH3)=C), 4.5 (1H, —OH)

(Synthesis Example 12-1) Synthesis of MAC-ADI4H4M

In 100 mL of toluene, 2.3 g (12.5 mmol) of 4-methyl-adamantane-1,4-diol was added with 11.2 g (50 mmol) of a 57% aqueous solution of hydrogen iodide, and the mixture was stirred at 80° C. for 8 hours to react. After the reaction, water was added, washing was performed with sodium hydrogen carbonate, and the organic layer was concentrated and then separated and purified by column chromatography to obtain 1.1 g of 1-iodo-4-methyl-4-hydroxyadamantane represented by the following formula.

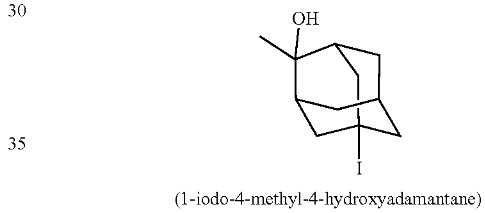

(1-iodo-4-methyl-4-hydroxyadamantane)

In the same manner as in Synthesis Example 9-1 except that 2.92 g (10 mmol) of 1-iodo-4-methyl-4-hydroxyadamantane obtained above was used instead of 2.78 g of 3-iodo-1-hydroxyadamantane, 3.1 g of an objective compound (MAC-ADI4H4M) represented by the following formula (MAC-ADI4H4M) was obtained.

When the obtained compound (MAC-ADI4H4M) was subjected to NMR measurement under the above measurement conditions, the following peaks were found, and it was confirmed that the compound had a chemical structure represented by the formula (MAC-ADI4H4M):

δ (ppm) (d-DMSO): 6.4-6.5 (2H, =CH2), 1.2-2.4 (19H, Ad-H, Ad-CH3, —C(CH3)=C)

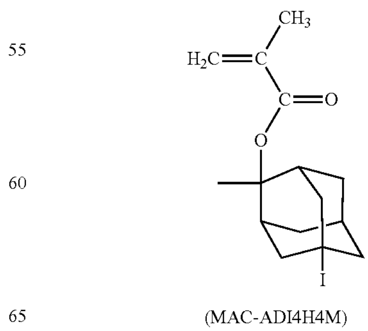

(MAC-ADI4H4M)

(Synthesis Example 13-1) Synthesis of ACLAC-ADI2

In a 300 mL eggplant flask equipped with a Dean Stark and reflux tube, 10.9 g (27 mmol) of 3,5-diiodo-1-hydroxy-adamantane was dissolved in 100 mL of toluene, 0.05 g (0.3 mmol) of p-toluene sulfonic acid was added under ice-cooling, and 2.9 g (27 mmol) of α-chloroacrylate was added dropwise thereto. Subsequently, the mixture was stirred and reacted under reflux conditions for 1 hour. After completion of the reaction, water was added to the reaction liquid, and the mixture was washed with aqueous sodium hydrogen carbonate solution. The organic phase was dried over magnesium sulfate, concentrated, and purified by column chromatography to obtain 8.9 g (yield: 65%) of the objective product ACLAC-ADI2 shown below.

When the obtained compound (ACLAC-ADI2) was subjected to NMR measurement under the above measurement conditions, the following peaks were found, and it was confirmed that the compound had a chemical structure represented by the formula (ACLAC-ADI2):

δ (ppm) ($CDCl_3$): 6.0-6.6 (2H, =CH2), 1.5-4.4 (13H, Ad-H)

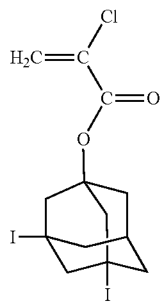

(ACLAC-AD12)

(Synthesis Working Example 1) Synthesis of MAC-4I Resin

In 45 mL of tetrahydrofuran, 1.5 g of MAC-4I, 3.0 g of 2-methyl-2-adamantyl methacrylate, 2.0 g of γ-butyrolactone methacrylate and 1.5 g of hydroxyadamantyl methacrylate were dissolved, and 0.20 g of azobisisobutyronitrile was added thereto. After refluxing for 12 hours, the reaction solution was added dropwise to 2 l of n-heptane. The deposited resin was filtered off and dried under reduced pressure to obtain a white powdery resin represented by the following chemical formula (P-MAC-4I). The resin had a molecular weight (Mw) of 12000 and a dispersity (Mw/Mn) of 1.90. As a result of measuring $^{13}$C-NMR, the composition ratio (molar ratio) in the following chemical formula (P-MAC-4I) was a:b:c:d=40:30:15:15. Although the chemical formula (P-MAC-4I) shown below is briefly described in order to indicate the ratio of each constituent unit, P-MAC-4I is not a block copolymer in which each constituent unit forms an independent block.

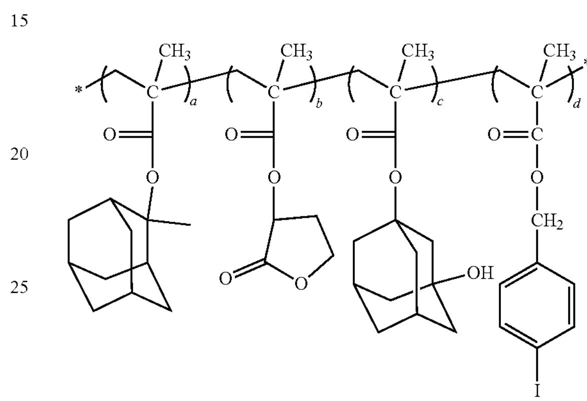

(P-MAC-41)

(Synthesis Working Example 2) Synthesis of MAC-2H35I Resin

In the same manner as in Synthesis Working Example 1 except that MAC-2H35I (2.2 g) was used instead of MAC-4I (1.5 g) in Synthesis Working Example 1, a resin represented by the following chemical formula (P-MAC-2H35I) was obtained. The resin had a molecular weight (Mw) of 14000 and a dispersity (Mw/Mn) of 2.0. As a result of measuring $^{13}$C-NMR, the composition ratio (molar ratio) in the following chemical formula (P-MAC-2H35I) was a:b:c:d=40:30:15:15. Although the chemical formula (P-MAC-2H35I) shown below is briefly described in order to indicate the ratio of each constituent unit, P-MAC-2H35I is not a block copolymer in which each constituent unit forms an independent block.

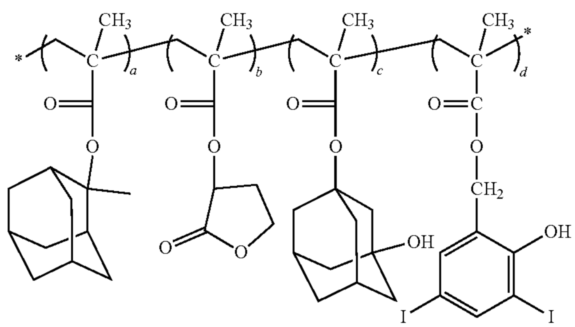

(P-MAC-2H351)

(Synthesis Working Example 3) Synthesis of MAC-4H35I Resin

In the same manner as in Synthesis Working Example 1 except that MAC-4H35I (2.2 g) was used instead of MAC-4I (1.5 g) in Synthesis Working Example 1, a resin represented by the following chemical formula (P-MAC-4H35I) was obtained. The resin had a molecular weight (Mw) of 14000 and a dispersity (Mw/Mn) of 2.0. As a result of measuring $^{13}$C-NMR, the composition ratio (molar ratio) in the following chemical formula (P-MAC-4H35I) was a:b:c:d=40:30:15:15. Although the chemical formula (P-MAC-4H35I) shown below is briefly described in order to indicate the ratio of each constituent unit, P-MAC-4H35I is not a block copolymer in which each constituent unit forms an independent block.

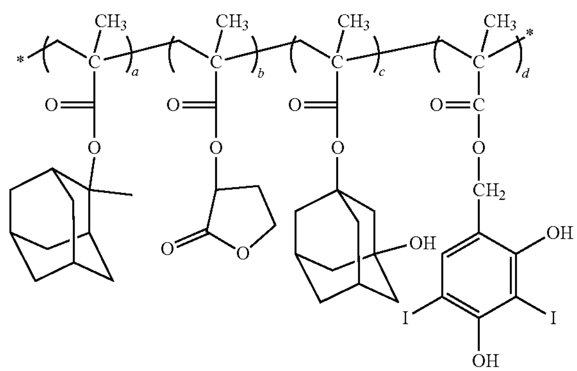

(P-MAC-4H351)

(Synthesis Working Example 4) Synthesis of MAC-2H35I-BOC Resin

In the same manner as in Synthesis Working Example 1 except that MAC-2H35I-BOC (2.7 g) was used instead of MAC-4I (1.5 g) in Synthesis Working Example 1, a resin represented by the following chemical formula (P-MAC-2H35I-BOC) was obtained. The resin had a molecular weight (Mw) of 14200 and a dispersity (Mw/Mn) of 2.0. As a result of measuring $^{13}$C-NMR, the composition ratio (molar ratio) in the following chemical formula (P-MAC-2H35I-BOC) was a:b:c:d=40:30:15:15. Although the chemical formula (P-MAC-2H35I-BOC) shown below is briefly described in order to indicate the ratio of each constituent unit, P-MAC-2H35I-BOC is not a block copolymer in which each constituent unit forms an independent block.

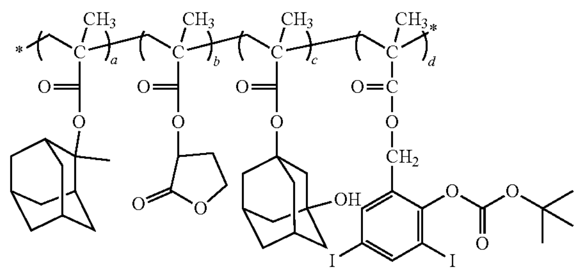

(P-MAC-2H351-BOC)

(Synthesis Working Example 5) Synthesis of MAC-2H35I-MeBOC Resin

In the same manner as in Synthesis Working Example 1 except that MAC-2H35I-MeBOC (2.8 g) was used instead of MAC-4I (1.5 g) in Synthesis Working Example 1, a resin represented by the following chemical formula (P-MAC-2H35I-MeBOC) was obtained. The resin had a molecular weight (Mw) of 14300 and a dispersity (Mw/Mn) of 2.0. As a result of measuring $^{13}$C-NMR, the composition ratio (molar ratio) in the following chemical formula (P-MAC-2H35I-MeBOC) was a:b:c:d=40:30:15:15. Although the chemical formula (P-MAC-2H35I-MeBOC) shown below is briefly described in order to indicate the ratio of each constituent unit, P-MAC-2H35I-MeBOC is not a block copolymer in which each constituent unit forms an independent block.

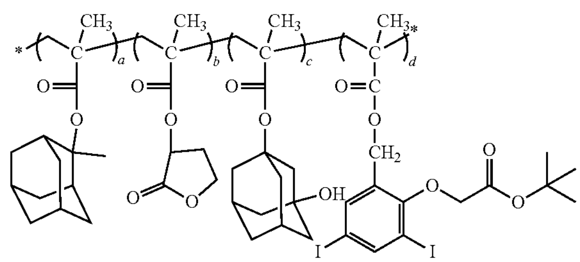

(P-MAC-2H351-MeBOC)

(Synthesis Working Example 6) Synthesis of MAC-4H35I-BOC Resin

In the same manner as in Synthesis Working Example 1 except that MAC-4H35I-BOC (2.7 g) was used instead of MAC-4I (1.5 g) in Synthesis Working Example 1, a resin represented by the following chemical formula (P-MAC-4H35I-BOC) was obtained. The resin had a molecular weight (Mw) of 14300 and a dispersity (Mw/Mn) of 2.0. As a result of measuring $^{13}$C-NMR, the composition ratio (molar ratio) in the following chemical formula (P-MAC-4H35I-BOC) was a:b:c:d=40:30:15:15. Although the chemical formula (P-MAC-4H35I-BOC) shown below is briefly described in order to indicate the ratio of each constituent unit, P-MAC-4H35I-BOC is not a block copolymer in which each constituent unit forms an independent block.

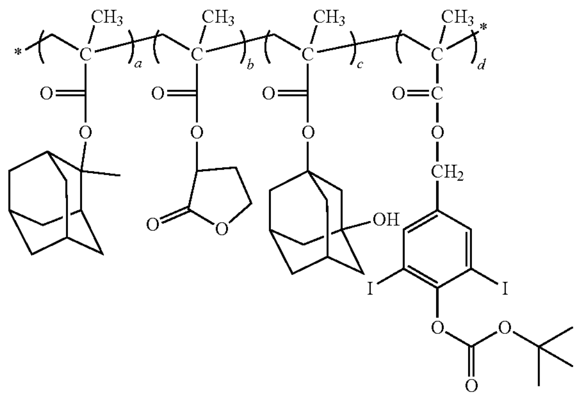

(P-MAC-4H351-BOC)

(Synthesis Working Example 7) Synthesis of MAC-4H35I-MeBOC Resin

In the same manner as in Synthesis Working Example 1 except that MAC-4H35I-MeBOC (2.8 g) was used instead of MAC-4I (1.5 g) in Synthesis Working Example 1, a resin represented by the following chemical formula (P-MAC-4H35I-MeBOC) was obtained. The resin had a molecular weight (Mw) of 14400 and a dispersity (Mw/Mn) of 2.0. As a result of measuring $^{13}C$-NMR, the composition ratio (molar ratio) in the following chemical formula (P-MAC-4H35I-MeBOC) was a:b:c:d=40:30:15:15. Although the chemical formula (P-MAC-4H35I-MeBOC) shown below is briefly described in order to indicate the ratio of each constituent unit, P-MAC-4H35I-MeBOC is not a block copolymer in which each constituent unit forms an independent block.

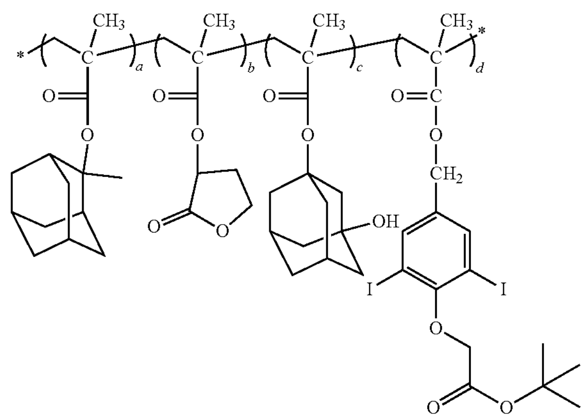

(P-MAC-4H351-MeBOC)

(Synthesis Working Example 8) Synthesis of MAC-ADI Resin

In the same manner as in Synthesis Working Example 1 except that MAC-ADI (1.8 g) was used instead of MAC-4I (1.5 g) in Synthesis Working Example 1, a resin represented by the following chemical formula (P-MAC-ADI) was obtained. The resin had a molecular weight (Mw) of 14400 and a dispersity (Mw/Mn) of 1.8. As a result of measuring $^{13}C$-NMR, the composition ratio (molar ratio) in the following chemical formula (P-MAC-ADI) was a:b:c:d=40:30:15:15. Although the chemical formula (P-MAC-ADI) shown below is briefly described in order to indicate the ratio of each constituent unit, P-MAC-ADI is not a block copolymer in which each constituent unit forms an independent block.

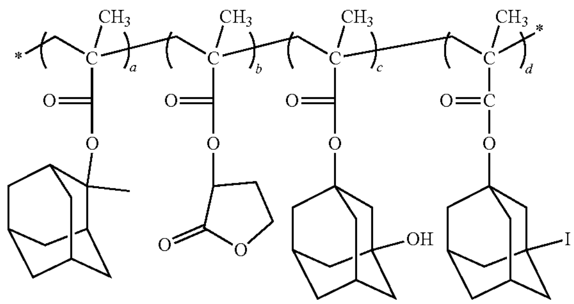

(P-MAC-ADI)

(Synthesis Working Example 9) Synthesis of MAC-ADI2 Resin

In the same manner as in Synthesis Working Example 1 except that MAC-ADI2 (2.4 g) was used instead of MAC-4I (1.5 g) in Synthesis Working Example 1, a resin represented by the following chemical formula (P-MAC-ADI2) was obtained. The resin had a molecular weight (Mw) of 14400 and a dispersity (Mw/Mn) of 1.8. As a result of measuring $^{13}$C-NMR, the composition ratio (molar ratio) in the following chemical formula (MAC-ADI2) was a:b:c:d=40:30:15:15. Although the chemical formula (P-MAC-ADI2) shown below is briefly described in order to indicate the ratio of each constituent unit, P-MAC-ADI2 is not a block copolymer in which each constituent unit forms an independent block.

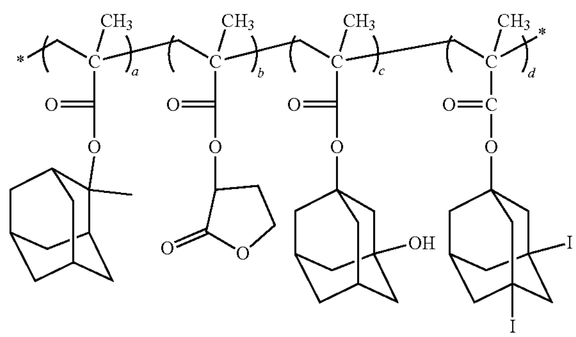

(P-MAC-ADI2)

(Synthesis Working Example 10) Synthesis of MAC-ADIOH Resin

In the same manner as in Synthesis Working Example 1 except that MAC-ADIOH (1.8 g) was used instead of MAC-4I (1.5 g) in Synthesis Working Example 1, a resin represented by the following chemical formula (P-MAC-ADIOH) was obtained. The resin had a molecular weight (Mw) of 14400 and a dispersity (Mw/Mn) of 1.7. As a result of measuring $^{13}$C-NMR, the composition ratio (molar ratio) in the following chemical formula (P-MAC-ADIOH) was a:b:c:d=40:30:15:15. Although the chemical formula (P-MAC-ADIOH) shown below is briefly described in order to indicate the ratio of each constituent unit, P-MAC-ADIOH is not a block copolymer in which each constituent unit forms an independent block.

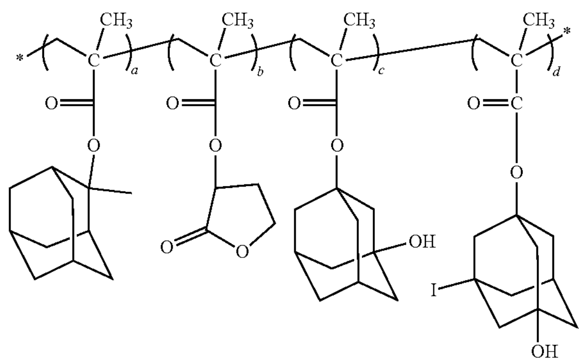

(P-MAC-ADI2)

(Synthesis Working Example 11) Synthesis of MAC-MADI Resin

Using 4.7 g of MAC-MADI, 2.0 g of γ-butyrolactone methacrylate and 3.0 g of hydroxyadamantyl methacrylate as monomer raw materials, a resin represented by the following chemical formula (P-MAC-MADI) was obtained in the same manner as in Synthesis Working Example 1. This resin had a molecular weight (Mw) of 14400 and a dispersity (Mw/Mn) of 1.9. As a result of measuring $^{13}$C-NMR, the composition ratio (molar ratio) in the following chemical formula (P-MAC-MADI) was a:b:c=40:30:30. Although the chemical formula (P-MAC-MADI) shown below is briefly described in order to indicate the ratio of each constituent unit, P-MAC-MADI is not a block copolymer in which each constituent unit forms an independent block.

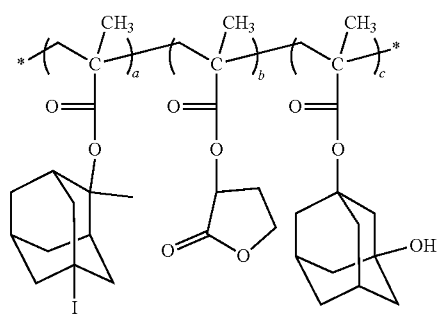

(P-MAC-MADI)

(Synthesis Working Example 12) Synthesis of MAC-MADI-ADIOH Resin

Using 2.5 g of MAC-ADIOH 1.8 g, 4.7 g of MAC-MADI, 2.0 g of γ-butyrolactone methacrylate, and 1.5 g of hydroxyadamantyl methacrylate as monomer raw materials, a resin represented by the following chemical formula (P-MAC-MADI-ADIOH) was obtained in the same manner as in Synthesis Working Example 1. The resin had a molecular weight (Mw) of 14400 and a dispersity (Mw/Mn) of 2.0. As a result of measuring $^{13}$C-NMR, the composition ratio (molar ratio) in the following chemical formula (P-MAC-MADI-ADIOH) was a:b:c:d=40:30:15:15. Although the chemical formula (P-MAC-MADI-ADIOH) shown below is briefly described in order to indicate the ratio of each constituent unit, P-MAC-MADI-ADIOH is not a block copolymer in which each constituent unit forms an independent block.

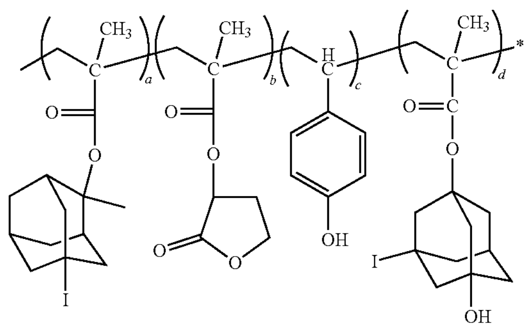

(P-MAC-MADI-ADIOH)

(Synthesis Working Example 13) Synthesis of MAC-MADI-ADIOH2 Resin

Except that 4.7 g of MAC-MADI, 2.0 g of γ-butyrolactone methacrylate and 3.6 g of MAC-ADIOH as monomer raw materials were used, a resin represented by the following chemical formula (P-MAC-MADI-ADIOH2) was obtained in the same manner as in Synthesis Working Example 1. The resin had a molecular weight (Mw) of 14400 and a dispersity (Mw/Mn) of 2.0. As a result of measuring $^{13}$C-NMR, the composition ratio (molar ratio) in the following chemical formula (P-MAC-MADI-ADIOH2) was a:b:c=40:30:30. Although the chemical formula (P-MAC-MADI-ADIOH2) shown below is briefly described in order to indicate the ratio of each constituent unit, P-MAC-MADI-ADIOH2 is not a block copolymer in which each constituent unit forms an independent block.

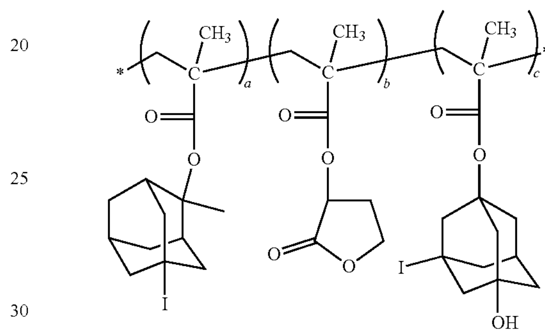

(P-MAC-MADI-ADIOH2)

(Synthesis Working Example 14) Synthesis of MAC-MADI-35IST Resin

Except that 4.7 g of MAC-MADI, 2.0 g of γ-butyrolactone methacrylate and 3.7 g of 3,5-diiodo-4-hydroxystyrene as monomer raw materials were used, a resin represented by the following chemical formula (P-MAC-MADI-35IST) was obtained in the same manner as in Synthesis Working Example 1. The resin had a molecular weight (Mw) of 14400 and a dispersity (Mw/Mn) of 2.0. As a result of measuring $^{13}$C-NMR, the composition ratio (molar ratio) in the following chemical formula (P-MAC-MADI-35IST) was a:b:c=40:30:30. Although the chemical formula (P-MAC-MADI-35IST) shown below is briefly described in order to indicate the ratio of each constituent unit, P-MAC-MADI-35IST is not a block copolymer in which each constituent unit forms an independent block.

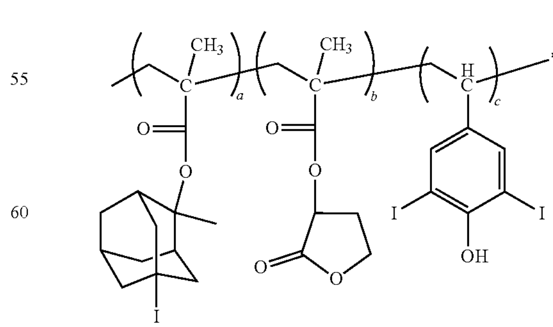

(P-MAC-MADI-35IST)

(Synthesis Working Example 15) Synthesis of MAC-MADI-35IST-ADIOH Resin

Except that 4.7 g of MAC-MADI, 2.0 g of γ-butyrolactone methacrylate, 1.9 g of 3,5-diiodo-4-hydroxystyrene, and 1.8 g of MAC-ADIOH as monomer raw materials were used, a resin represented by the following chemical formula (P-MAC-MADI-35IST-ADIOH) was obtained in the same manner as in Synthesis Working Example 1. The resin had a molecular weight (Mw) of 14400 and a dispersity (Mw/Mn) of 2.0. As a result of measuring $^{13}C$-NMR, the composition ratio (molar ratio) in the following chemical formula (P-MAC-MADI-35IST-ADIOH) was a:b:c:d=40:30:15:15. Although the chemical formula (P-MAC-MADI-35IST-ADIOH) shown below is briefly described in order to indicate the ratio of each constituent unit, P-MAC-MADI-35IST-ADIOH is not a block copolymer in which each constituent unit forms an independent block.

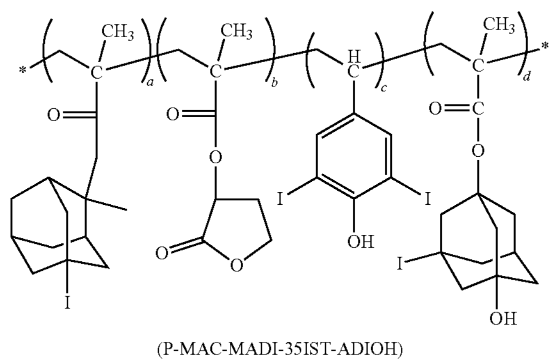

(P-MAC-MADI-35IST-ADIOH)

(Synthesis Working Example 16) Synthesis of MAC-ADIOH-CLMAA Resin

Except that 8.1 g of MAC-ADI0H and 1.9 g of methyl 2-chloroacrylate as monomer raw materials were used, a resin represented by the following chemical formula (P-MAC-ADIOH-CLMAA) was obtained in the same manner as in Synthesis Working Example 1. The resin had a molecular weight (Mw) of 14400 and a dispersity (Mw/Mn) of 2.0. As a result of measuring $^{13}C$-NMR, the composition ratio (molar ratio) in the following chemical formula (P-MAC-ADIOH-CLMAA) was a:b=50:50. Although the chemical formula (P-MAC-ADIOH-CLMAA) shown below is briefly described in order to indicate the ratio of each constituent unit, P-MAC-MADIOH-CLMAA is not a block copolymer in which each constituent unit forms an independent block.

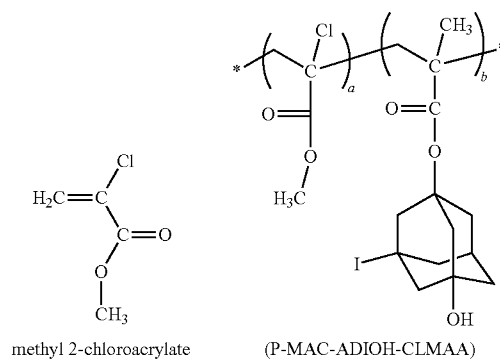

methyl 2-chloroacrylate (P-MAC-ADIOH-CLMAA)

(Synthesis Working Example 17) Synthesis of MAC-4H35I-CLMAA Resin

Except that 7.4 g of MAC-4H35I and 1.9 g of methyl 2-chloroacrylate as monomer raw materials were used, a resin represented by the following chemical formula (P-MAC-4H35I-CLMAA) was obtained in the same manner as in Synthesis Working Example 1. The resin had a molecular weight (Mw) of 14400 and a dispersity (Mw/Mn) of 2.0. As a result of measuring $^{13}C$-NMR, the composition ratio (molar ratio) in the following chemical formula (P-MAC-4H35I-CLMAA) was a:b=50:50. Although the chemical formula (P-MAC-4H35I-CLMAA) shown below is briefly described in order to indicate the ratio of each constituent unit, P-MAC-4H35I-CLMAA is not a block copolymer in which each constituent unit forms an independent block.

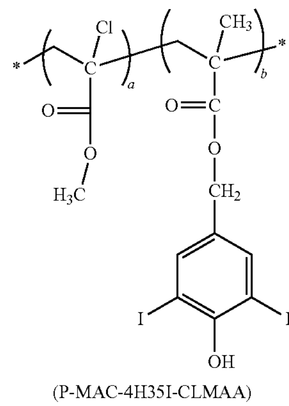

(P-MAC-4H35I-CLMAA)

(Synthesis Working Example 18) Synthesis of MAC-ADI2-4H35I Resin

Except that 3.9 g of MAC-ADI2, 3.7 g of MAC-4H35I, and 1.9 g of methyl 2-chloroacrylate as monomer raw materials were used, a resin represented by the following chemical formula (P-MAC-ADI2-4H35I) was obtained in the same manner as in Synthesis Working Example 1. The resin had a molecular weight (Mw) of 14400 and a dispersity (Mw/Mn) of 2.0. As a result of measuring $^{13}C$-NMR, the composition ratio (molar ratio) in the following chemical formula (P-MAC-ADI2-4H35I) was a:b:c=25:25:50. Although the chemical formula (P-MAC-ADI2-4H35I) shown below is briefly described in order to indicate the ratio of each constituent unit, P-MAC-ADI2-4H35I is not a block copolymer in which each constituent unit forms an independent block.

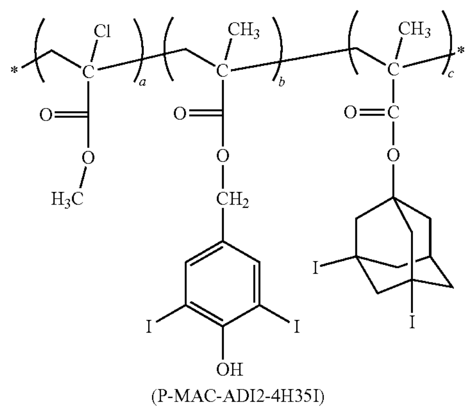

(P-MAC-ADI2-4H35I)

(Synthesis Working Example 19) Synthesis of ACLAC-2H35I-AMST Resin

Except that 7.4 g of ACLAC-2H35I and 1.9 g of α-methylstyrene as monomer raw materials were used, a resin represented by the following chemical formula (P-ACLAC-2H35I-AMST) was obtained in the same manner as in Synthesis Working Example 1. The resin had a molecular weight (Mw) of 14400 and a dispersity (Mw/Mn) of 2.0. As a result of measuring $^{13}C$-NMR, the composition ratio (molar ratio) in the following chemical formula (P-ACLAC-2H35I-AMST) was a:b=50:50. Although the chemical formula (P-ACLAC-2H35I-AMST) shown below is briefly described in order to indicate the ratio of each constituent unit, P-ACLAC-2H35I-AMST is not a block copolymer in which each constituent unit forms an independent block.

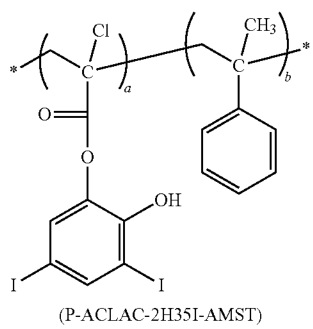

(P-ACLAC-2H35I-AMST)

(Synthesis Working Example 20) Synthesis of MAC-4H35I-ACLAC-2H35I Resin

Except that 7.4 g of MAC-4H35I and 7.4 g of ACLAC-2H35I as monomer raw materials were used, a resin represented by the following chemical formula (P-MAC-4H35I-ACLAC-2H35I) was obtained in the same manner as in Synthesis Working Example 1. The resin had a molecular weight (Mw) of 14400 and a dispersity (Mw/Mn) of 2.0. As a result of measuring $^{13}C$-NMR, the composition ratio (molar ratio) in the following chemical formula (P-MAC-4H35I-ACLAC-2H35I) was a:b=50:50. Although the chemical formula (P-MAC-4H35I-ACLAC-2H35I) shown below is briefly described in order to indicate the ratio of each constituent unit, P-MAC-4H35I-ACLAC-2H35I is not a block copolymer in which each constituent unit forms an independent block.

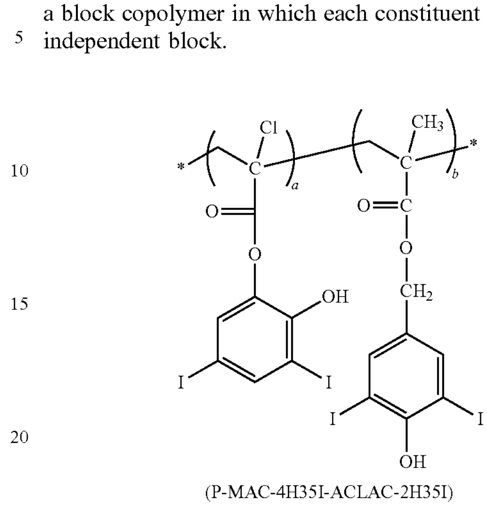

(P-MAC-4H35I-ACLAC-2H35I)

(Synthesis Working Example 21) Synthesis of ACLAC-ADI2-AMST Resin

Except that 7.9 g of ACLAC-ADI2 and 1.9 g of α-methylstyrene as monomer raw materials were used, a resin represented by the following chemical formula (P-ACLAC-ADI2-AMST) was obtained in the same manner as in Synthesis Working Example 1. The resin had a molecular weight (Mw) of 14400 and a dispersity (Mw/Mn) of 2.0. As a result of measuring $^{13}C$-NMR, the composition ratio (molar ratio) in the following chemical formula (P-ACLAC-ADI2-AMST) was a:b=50:50. Although the chemical formula (P-ACLAC-ADI2-AMST) shown below is briefly described in order to indicate the ratio of each constituent unit, P-ACLAC-ADI2-AMST is not a block copolymer in which each constituent unit forms an independent block.

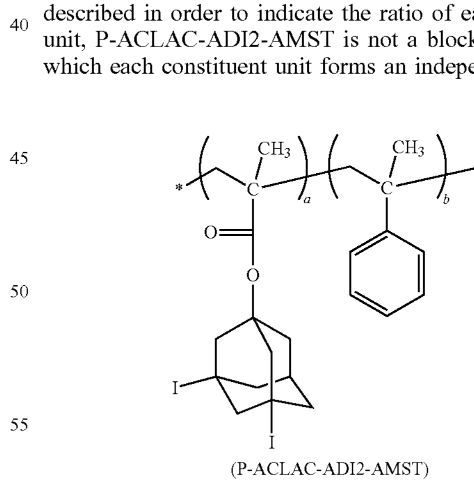

(P-ACLAC-ADI2-AMST)

Synthesis Comparative Example 1

A resin represented by the following chemical formula (P-AC-1) was obtained in the same manner as in Synthesis Working Example 1 except that MAC-4I was not used. The resin had a molecular weight (Mw) of 13500 and a dispersity (Mw/Mn) of 2.30.

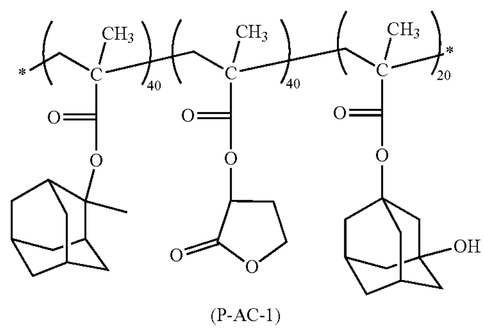

(P-AC-1)

In the formula (P-AC-1), "40", "40", and "20" indicate molar ratios of the constituent units. Although the formula (P-AC-1) is briefly described in order to indicate the ratio of each constituent unit, P-AC-1 is not a block copolymer in which each constituent unit forms an independent block.

Example 1

The MAC-4I resin (P-MAC-4I) solution was applied onto a silicon wafer and baked at 110 to 130° C. for 60 seconds to form a photoresist layer having a film thickness of 100 nm. Here, the resin solution was prepared by compounding 5 parts by mass of the resin represented by the chemical formula (P-MAC-4I), 1 part by mass of triphenylsulfonium nonafluoromethanesulfonate, 0.1 parts by mass of tributylamine, and 92 parts by mass of PGMEA.

Subsequently, the resist film was exposed using an electron beam lithography system (manufactured by ELIONIX INC.; ELS-7500, 50 keV), baked (PEB) at 115° C. for 90 seconds, and developed for 60 seconds in a 2.38% by mass tetramethylammonium hydroxide (TMAH) aqueous solution to obtain a positive type pattern. The resolution and sensitivity results are shown in Table 1.

Example 2

A photoresist layer was formed in the same manner as in Example 1 except that MAC-2H35I resin (P-MAC-2H35I) solution was used instead of MAC-4I resin (P-MAC-4I) solution. The resolution and sensitivity results are shown in Table 1.

Example 3

A photoresist layer was formed in the same manner as in Example 1 except that MAC-4H35I resin (P-MAC-4H35I) solution was used instead of MAC-4I resin (P-MAC-4I) solution. The resolution and sensitivity results are shown in Table 1.

Comparative Example 1

A resin solution was prepared in the same manner as in Example 1 except that the resin of the chemical formula (P-AC-1) was used instead of the resin of the chemical formula (P-MAC-4I) in the resin solution to form a photoresist layer. A positive pattern was obtained by developing in the same manner as in Example 1. The resolution and sensitivity results are shown in Table 1.

(Aging)

The resin solution for forming the resist layer thus prepared was subjected to an aging test at 40° C. for 30 days in a state of being filled in a light-shielding bottle, and defects after aging were evaluated by the following method.

That is, the resin solutions for forming a resist layer before and after the aging test were respectively applied to different silicon wafers by a spin coater, and further heated on a hotplate at 110° C. for 1 minute to form a resist layer having a film thickness of 80 nm.

Then, after performing a maskless shot exposure with an increased exposure amount from 1 mJ/cm$^2$ to 80 mJ/cm$^2$ by 1 mJ/cm$^2$ at a time over the entire surface of the wafer using an extreme ultraviolet (EUV) exposure apparatus "EUVES-7000" (product name, manufactured by Lithotech Japan Co., Ltd.), the wafer was baked at 110° C. for 90 seconds (PEB), developed with isoamyl acetate for 60 seconds, and a wafer on which a shot exposure for 80 shots was performed was obtained. The film thickness of each shot exposure area thus obtained was measured by an optical interference film thickness meter "VM 3200" (product name, manufactured by SCREEN Semiconductor Solutions Co., Ltd.), profile data of the film thickness with respect to the exposure amount was obtained, and the exposure amount at which the gradient of the film thickness variation amount with respect to the exposure amount became the largest was calculated as a sensitivity value (mJ/cm$^2$), and used as an index of the EUV sensitivity of the resist.

Furthermore, the sensitivity of the resin solution for forming the resist layer was evaluated before and after the aging test at 40° C. for 30 days, and the rate of change in sensitivity before and after the aging test was determined by the following index.

"variation rate"=[("sensitivity of resin solution before aging"−"sensitivity of resin solution after aging")/"sensitivity of resin solution before aging"]×100

A variation rate is less than 2%

B variation rate is 2% or more and less than 5%

C variation rate is 5% or more and less than 10%

D variation is 10% or more

TABLE 1

| | Resin | Resolution | Sensitivity | Aging |
|---|---|---|---|---|
| Example 1 | P-MAC-4I | 40 nm L/S | 12 μC/cm$^2$ | A |
| Example 2 | P-MAC-2H35I | 40 nm L/S | 10 μC/cm$^2$ | B |
| Example 3 | P-MAC-4H35I | 40 nm L/S | 10 μC/cm$^2$ | A |
| Example 4 | P-MAC-2H35I-Boc | 40 nm L/S | 10 μC/cm$^2$ | B |
| Example 5 | P-MAC-2H35I-MeBOC | 40 nm L/S | 10 μC/cm$^2$ | B |
| Example 6 | P-MAC-4H35I-BOC | 40 nm L/S | 10 μC/cm$^2$ | A |
| Example 7 | P-MAC-4H35I-MeBOC | 40 nm L/S | 10 μC/cm$^2$ | A |
| Example 8 | P-MAC-ADI | 40 nm L/S | 12 μC/cm$^2$ | A |
| Example 9 | P-MAC-ADI2 | 40 nm L/S | 10 μC/cm$^2$ | A |
| Example 10 | P-MAC-ADIOH | 40 nm L/S | 11 μC/cm$^2$ | A |
| Example 11 | P-MAC-MADI | 40 nm L/S | 10 μC/cm$^2$ | B |
| Example 12 | P-MAC-MADI-ADIOH | 40 nm L/S | 10 μC/cm$^2$ | A |
| Example 13 | P-MAC-MADI-ADIOH2 | 40 nm L/S | 9 μC/cm$^2$ | A |
| Example 14 | P-MAC-MADI-35IST | 40 nm L/S | 8 μC/cm$^2$ | A |
| Example 15 | P-MAC-MADI-35IST-ADIOH | 40 nm L/S | 8 μC/cm$^2$ | A |
| Comparative Example 1 | P-AC-1 | 80 nm L/S | 26 μC/cm$^2$ | B |

Example 16

(Evaluation of Resolution)

The P-MAC-ADIOH-CLMMA resin (P-MAC-ADIOH-CLMMA) solution described in Synthesis Working Example 16 was applied onto a silicon wafer and baked at 110° C. for 60 seconds to form a photoresist layer having a film thickness of 100 nm. Here, the resin solution was prepared by compounding 7 parts by mass of the resin represented by the chemical formula (P-MAC-ADIOH-CLMMA) and 93.9 parts by mass of the PGMEA.

Subsequently, the resist film was exposed using an electron beam lithography system (manufactured by ELIONIX INC.; ELS-7500, 50 keV), baked (PEB) at 115° C. for 90 seconds, and developed for 60 seconds using isoamyl acetate as a developer to obtain a positive type pattern. The resolution and sensitivity results are shown in Table 2.

(Aging)

Using the P-MAC-ADIOH-CLMMA resin (P-MAC-ADIOH-CLMMA) solution described in Synthesis Working Example 16, the same resin solution was prepared before and after 30 days of aging in a light-shielded state at 40° C., with the exception of the presence or absence of aging treatment, and each resin solution was formed on a wafer by spin coater, followed by development treatment using isoamyl acetate as a developer, the sensitivity before and after aging was determined, and the aging performance was evaluated by deriving the rate of change according to the following indexes.

"variation rate"=[("sensitivity of resin solution before aging"−"sensitivity of resin solution after aging")/"sensitivity of resin solution before aging"]×100

A variation amount is less than 2%

B variation rate is 2% or more and less than 5%

C variation rate is 5% or more and less than 10%

D variation is 10% or more

The same evaluation was performed for the materials of Synthesis Working Example 17 and subsequent examples. The results are shown in Table.

TABLE 2

| | Resin | Resolution | Sensitivity | Aging |
|---|---|---|---|---|
| Example 16 | P-MAC-ADIOH-CLMAA | 40 nm L/S | 16 μC/cm$^2$ | A |
| Example 17 | P-MAC-4H35I-CLMAA | 40 nm L/S | 15 μC/cm$^2$ | B |
| Example 18 | P-MAC-ADI2-4H35I | 40 nm L/S | 15 μC/cm$^2$ | A |
| Example 19 | P-ACLAC-2H35I-AMST | 40 nm L/S | 14 μC/cm$^2$ | A |
| Example 20 | P-MAC-4H35I-ACLAC-2H35I | 40 nm L/S | 13 μC/cm$^2$ | B |
| Example 21 | P-ACLAC-ADI2-AMST | 40 nm L/S | 13 μC/cm$^2$ | A |

As described above, by using the iodine-containing (meth)acrylate compound and/or the iodine-containing (meth)acrylate (co)polymer of the present embodiment, a composition capable of forming a lithography film with high resolution and high sensitivity can be obtained.

According to the present invention, it is possible to provide a compound and a composition capable of forming a film having high resolution and sensitivity, as well as a method for forming a resist pattern and a method for forming an insulating film, using these.

The invention claimed is:

1. An iodine-containing (meth) acrylate compound represented by the general formula (1):

(1)

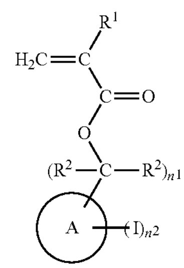

wherein $R^1$ represents a hydrogen atom, methyl, or a halogen atom;

each $R^2$ independently represents a hydrogen atom;

A represents an optionally substituted arene having 5 to 30 carbon atoms;

$n^1$ represents 1; and $n^2$ represents an integer of 2 to 20.

2. An iodine-containing (meth)acrylate (co)polymer having a repeating unit represented by the general formula (4):

(4)

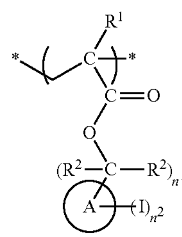

wherein $R^1$ represents a hydrogen atom, a methyl group, or halogen;

each $R^2$ independently represents a hydrogen atom;

A represents an optionally substituted arene having 5 to 30 carbon atoms;

$n^1$ represents 1;

$n^2$ represents an integer of 2 to 20; and symbol * represents a bonding site to an adjacent repeating unit.

3. A composition comprising the iodine-containing (meth) acrylate (co)polymer according to claim 2.

4. The composition according to claim 3, further comprising a solvent.

5. The composition according to claim 3, further comprising an acid generating agent.

6. The composition according to claim 3, further comprising an acid diffusion controlling agent.

7. A method for forming a pattern, comprising the steps of:

forming a film using the composition according to claim 3;

exposing the film; and forming a pattern by removing an exposed portion of the exposed film by using a developer.

8. A method for producing the iodine-containing (meth) acrylate compound according to claim 1, comprising the step of reacting an iodine-containing hydroxy compound represented by the general formula (a) with a (meth)acrylic acid compound represented by the general formula (b):

(a)

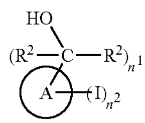

wherein each $R^2$ independently represents a hydrogen atom;

A represents an optionally substituted arene having 5 to 30 carbon atoms;

$n^1$ represents 1; and $n^2$ represents an integer of 2 to 20;

(b)

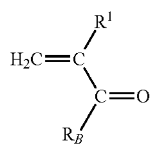

wherein $R^1$ represents a hydrogen atom, methyl, or a halogen atom; and $R_B$ is selected from the group consisting of a hydroxyl group, a halogen atom, and an (meth)acryloyloxy group.

9. The method for producing the iodine-containing (meth) acrylate compound according to claim 8, further comprising the step of performing an iodine introduction reaction to a compound represented by the following general formula (Sa1) or general formula (Sa2):

(Sa1)

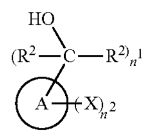

wherein each $R^2$ independently represents a hydrogen atom;

A represents an optionally substituted arene having 5 to 30 carbon atoms;

$n^1$ represents 1;

$n^2$ represents an integer of 2 to 20; and

X is selected from the group consisting of a hydroxy group; an aliphatic group having 1 to 30 carbon atoms or an aromatic group, the aliphatic group or the aromatic group having at least one selected from the group consisting of a hydroxy group, an aldehyde group and a carboxyl group; or a halogen atom;

(Sa2)

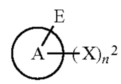

wherein

A represents an optionally substituted arene having 5 to 30 carbon atoms;

$n^2$ represents an integer of 2 to 20;

X is as defined in the formula (Sa1); and

E is a hydrocarbon group having 1 to 30 carbon atoms and having at least one selected from the group consisting of a hydroxy group, an aldehyde group, a carboxyl group, an ether group, a thiol group, and an amino group.

* * * * *